US 11,351,034 B2

(12) United States Patent
Satterthwaite et al.

(10) Patent No.: US 11,351,034 B2
(45) Date of Patent: Jun. 7, 2022

(54) PATIENT SPECIFIC FEMORAL PROSTHESIS

(71) Applicant: DePuy Synthes Products, Inc., Raynham, MA (US)

(72) Inventors: Rodney E. Satterthwaite, Huntington, IN (US); Jeffrey A. McAnelly, Churubusco, IN (US); Andrew M. Jacobs, Ft. Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 176 days.

(21) Appl. No.: 16/587,683

(22) Filed: Sep. 30, 2019

(65) Prior Publication Data

US 2021/0093459 A1    Apr. 1, 2021

(51) Int. Cl.
*A61F 2/36* (2006.01)
*A61F 2/30* (2006.01)
*A61B 17/72* (2006.01)

(52) U.S. Cl.
CPC ............ *A61F 2/367* (2013.01); *A61F 2/3672* (2013.01); *A61B 17/72* (2013.01); *A61F 2002/30069* (2013.01); *A61F 2002/30538* (2013.01); *A61F 2002/30784* (2013.01); *A61F 2002/30919* (2013.01); *A61F 2002/3611* (2013.01); *A61F 2002/3625* (2013.01)

(58) Field of Classification Search
CPC combination set(s) only.
See application file for complete search history.

(56) References Cited

U.S. PATENT DOCUMENTS

| 4,012,796 | A |   | 3/1977 | Weisman et al. |
|-----------|---|---|--------|----------------|
| 4,167,047 | A | * | 9/1979 | Grundei ............... A61F 2/3662 623/20.34 |
| 4,406,023 | A | * | 9/1983 | Harris ................. A61F 2/30767 623/23.29 |
| 4,728,335 | A | * | 3/1988 | Jurgutis ............. A61F 2/30734 623/23.23 |
| 4,770,660 | A |   | 9/1988 | Averill |

(Continued)

FOREIGN PATENT DOCUMENTS

| EP | 0216489 A1 | 4/1987 |
| FR | 2863866 A1 | 6/2005 |
| JP | 2002-038201 A | 2/2002 |

OTHER PUBLICATIONS

Braten et al., Femoral anteversion in normal adults, Acta Orthop Scand. 1992; 63(1): 29-32.

(Continued)

*Primary Examiner* — Yashita Sharma
(74) *Attorney, Agent, or Firm* — BakerHostetler

(57) ABSTRACT

A femoral prosthesis system for an orthopaedic hip implant and method of use is disclosed. The prosthesis system includes a femoral stem component that includes a core body and a casing that encases the core body. The casing can be additively manufactured such that the core body defines a predetermined orientation in the core body among a plurality of permissible predetermined orientations. The femoral stem component can further include a neck and a trunnion that extends from the neck. The neck can extend out with respect to the core body at a predetermined angle within a range of permissible predetermined angles.

16 Claims, 12 Drawing Sheets

(56) References Cited

U.S. PATENT DOCUMENTS

| | | | |
|---|---|---|---|
| 4,827,919 | A | 5/1989 | Barbarito et al. |
| 5,116,377 | A | 5/1992 | Skripitz et al. |
| 5,201,769 | A | 4/1993 | Schutzer |
| 5,376,124 | A | 12/1994 | Gustke et al. |
| 5,766,262 | A | 6/1998 | Mikhail |
| 6,027,682 | A | 2/2000 | Almquist et al. |
| 7,261,741 | B2 | 8/2007 | Weissman et al. |
| 7,537,664 | B2 | 5/2009 | O'Neill et al. |
| 8,268,099 | B2 | 9/2012 | O'Neill et al. |
| 8,269,100 | B2 | 9/2012 | Darling et al. |
| 8,530,560 | B2 | 9/2013 | Kerr et al. |
| 8,590,157 | B2 | 11/2013 | Kruth et al. |
| 8,992,703 | B2 | 3/2015 | O'Neill et al. |
| 9,456,901 | B2 | 10/2016 | Jones et al. |
| 10,213,310 | B2 | 2/2019 | Armacost et al. |
| 10,213,314 | B2 | 2/2019 | Armacost et al. |
| 10,251,752 | B2 | 4/2019 | Satterthwaite et al. |
| 10,399,147 | B2 | 9/2019 | Scott et al. |
| 2003/0109933 | A1 | 6/2003 | Weissman et al. |
| 2007/0067042 | A1 | 3/2007 | Weissman et al. |
| 2009/0222091 | A1 | 9/2009 | Morrissette et al. |
| 2012/0323339 | A1 | 12/2012 | Olalde et al. |

OTHER PUBLICATIONS

Charles, et al., Soft-Tissue Balancing of the Hip; The Role of Femoral Offset Restoration; Journal of Bone & Joint Surgery, vol. 86A, No. 5, May 2004, 1078-1088.

EP Search Report for European Patent Application No. 16203841.8-1664, dated May 19, 2017, 9 pages.

Garden, The Structure and Function of the Proximal End of the Femur; The Journal of Bone and Joint Surgery, vol. 43B, No. 3, Aug. 1961, 576-589.

Spitzer, The Cemented Femoral Stem: Selecting the Ideal Patient; Orthopedics (Supplement), vol. 28, No. 8, Aug. 2005, s841-s848.

U.S. Appl. No. 16/365,557, filed Mar. 26, 2019 entitled "Patient Specific Femoral Prosthesis".

Bobyn et al., "Characteristics of bone ingrowth and interface mechanics of a new porous tantalum biomaterials", The journal of Bone & Joint Surgery, Sep. 1999, vol. 81-B, No. 5, 907-914.

Chua et al., "Development of a Tissue Engineering Scaffold Structure Library for Rapid Prototyping, Part 1: Investigation and Classification", Intl. Journal Adv. Manuf. Technol., 2003, 21, 291-301.

Chua et al., "Development of a Tissue Engineering Scaffold Structure Library for Rapid Prototyping Part 2: Parametric Library and Assembly Program", Int. J. Adv. Manuf. Technol., 2003, 21, 302-312.

Hong et al., "A New Ti—5Ag Alloy for Customized Prostheses by Three-dimensional printing (3DPtm)", Research Reports, Biomaterials & Bioengineering, J. Dent. Res., 2001, 80(3), 860-863.

Meiners et al., "Direct Generation of Metal Parts and Tools by Selective Laser Powder Remelting (SLPR)", Fraunhofer Institute for Laser Technologies (ILT), 1999, 655-662.

Morgan et al., "Direct Metal Laser Re-Melting (DMLR) of 316L Stainless Steel Powder, Part 1: Analysis of Thin Wall Structures", Research in Advanced Technologies Group, Faculty of Engineering, The University of Liverpool, UK, 2001, 276-282.

Morgan et al., "Direct Metal Laser Re-Melting of 316L Stainless Steel Powder, part 2: Analysis of Cubic Primitives", Research in Advanced Technologies Group, Faculty of Engineering, The University of Liverpool, UK, 2001, 283-295.

Morgan et al., "Experimental Investigation of Nanosecond pulsed: Nd:YAG laser re-melted pre-placed powder beds", Rapid Prototyping Journal, 2001, vol. 7, No. 3, 159-172.

Morgan et al., "High Density net shape components by direct laser re-melting of single-phase powders", Journal of Materials Science, 2002, 37, 3093-3100.

Mullen et al., "Selective Laser Melting: A Unit Cell Approach for the Manufacture of Porous, Titanium, Bone-Ingrowth Constructs, Suitable for Orthopedic Applications, II, Randomized Structures", Journal of Biomedical Materials Research, Part B: Applied Biomaterials, Jan. 2010, 178-188.

Pogson et al., "The Production of Copper parts using DMLR", Rapid Prototyping Journal, 2003, vol. 9, No. 5, 334-343.

Ramos et al., "Mechanics of the Selective Laser Raster-Scanning Surface Interaction", Department of Mechanical and Metallurgical Engineering, Pontificia Universidad, Chile, Department of Mechanical Engineering, University of Texas at Austin, Aug. 2003, 559-572.

Williams et al., "Advances in Modeling the effects of selected parameters on the SLS process", Rapid Prototyping Journal, 1998, vol. 4, No. 2, 90-100.

Williams et al., "Selective Laser Sintering Part Strength as a Function of Andrew Number, Scan Rate and Spot Size", Clemson University, 1996, 10 pages.

Wysocki et al., "Laser and Electron Beam Additive Manufacturing Methods of Fabricating Titanium Bone Implants", Applied Sciences, 2017, 7, 657, 20 pages.

Yang et al., "The Design of scaffolds for use in tissue engineering, Part 1, Traditional Factors", Tissue Engineering, Dec. 2001, vol. 7(6), 679-689.

Yang et al., "The Design of Scaffolds for use in Tissue Engineering, Part II, Rapid Prototyping Techniques", Tissue Engineering, Feb. 2002, vol. 8(1), 1-11.

* cited by examiner

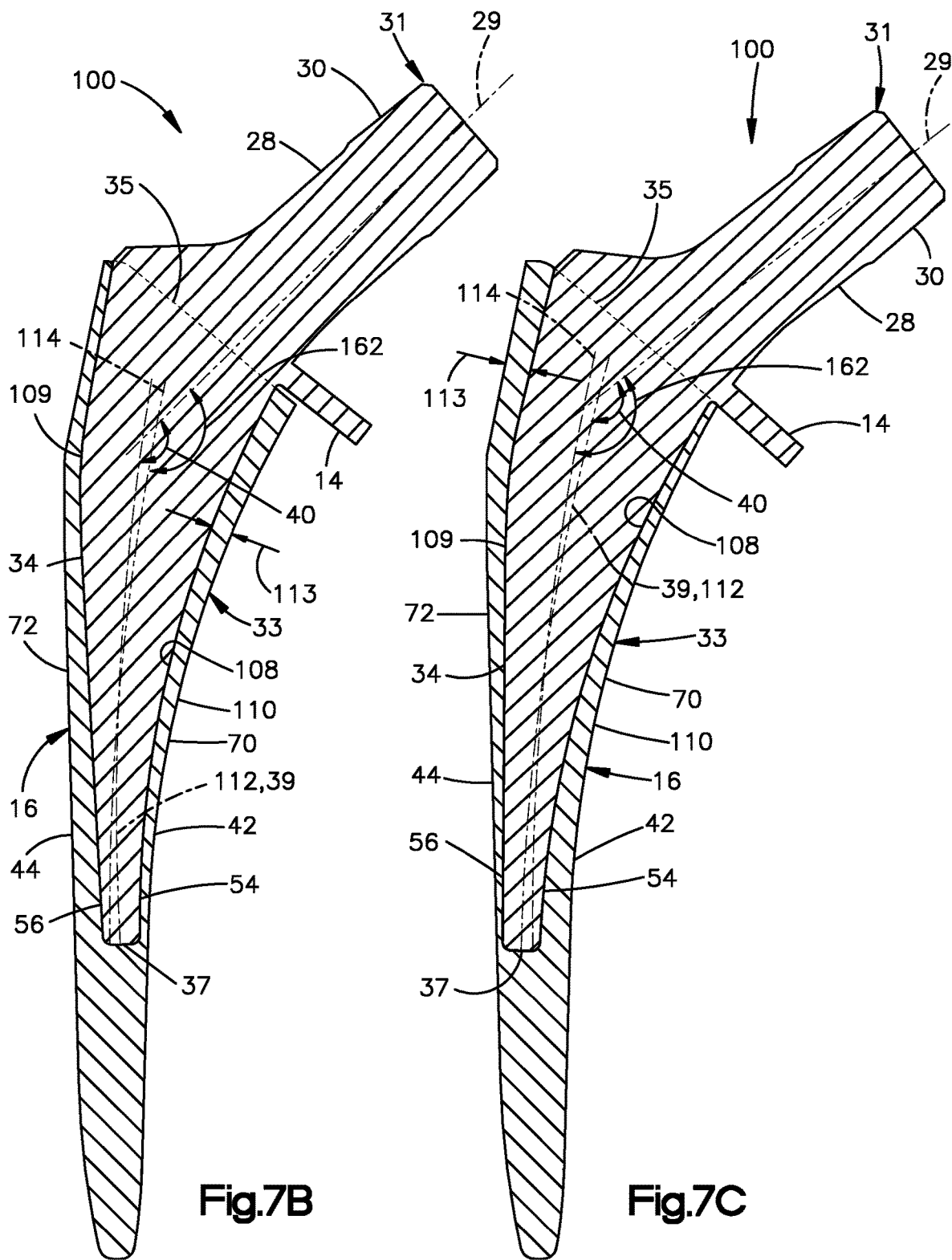

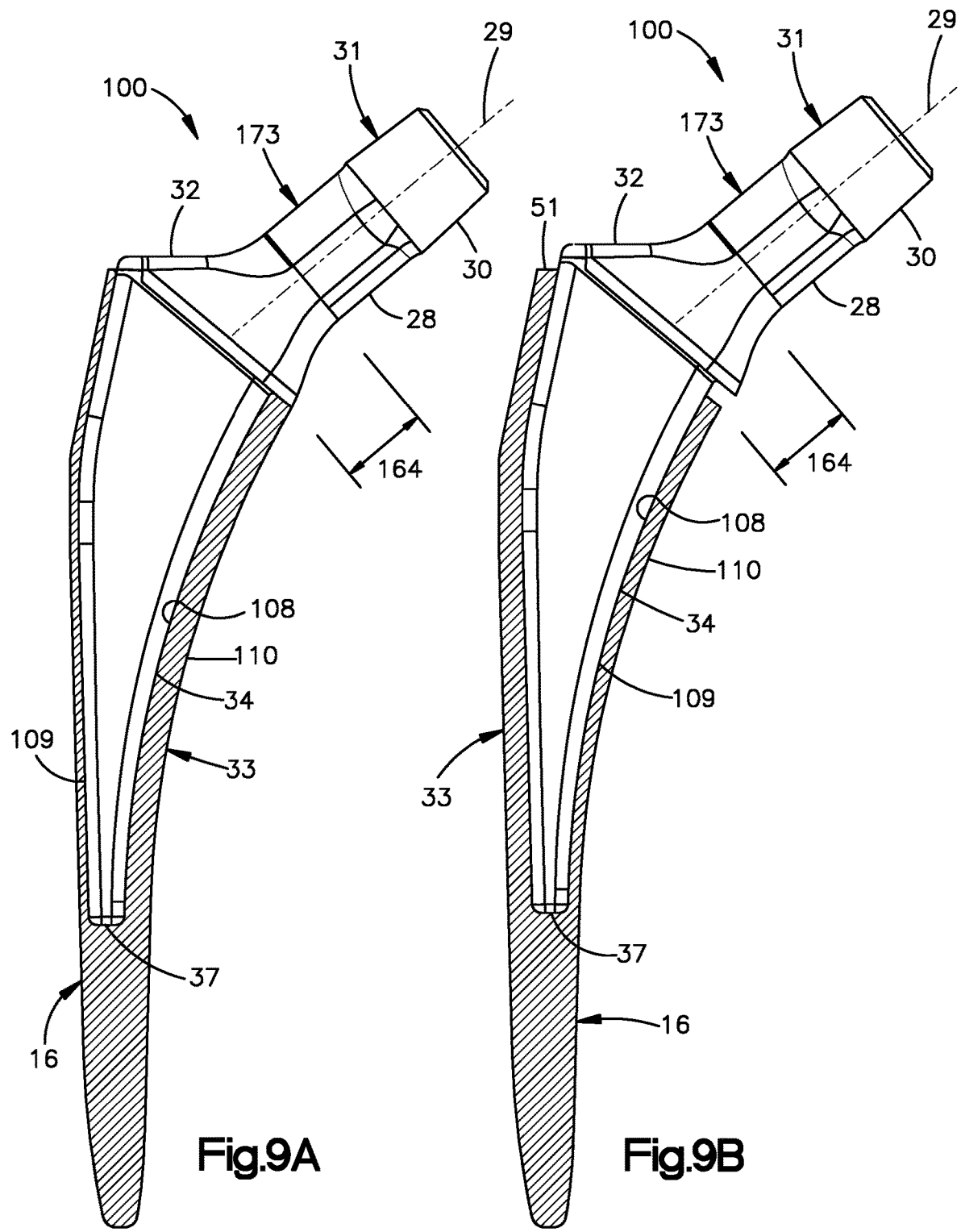

PATIENT SPECIFIC FEMORAL PROSTHESIS

TECHNICAL FIELD

The present disclosure relates generally to customizable femoral components used in a total hip arthroplasty and more particularly to one or more collars that may be coupled to a femoral stem of a hip prosthesis.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer bearing or ring.

A typical femoral component includes a stem having a neck and an elongate body extending distally from the neck, and a femoral head configured to be positioned on the neck of the stem. The stem of the femoral component is secured to a patient's femur. For instance, the stem can be surrounded by an outer sleeve that defines an outer surface of the femoral component in the medullary canal of the femur. The femoral head can articulate in the acetabular cup to replicate the motion of a natural hip joint.

Examples of hip prostheses are shown and described in U.S. Pat. Nos. 10,213,314 and 10,213,310

SUMMARY

In one example, a femoral prosthesis includes an elongate core body that extends along a central core body axis from a proximal core body end to a distal core body end opposite the proximal core body end. The core body includes a medial core body side and a lateral core body side opposite the medial core body side. The medial and lateral core body sides extend from the proximal core body end to the distal core body end. The core body is configured to be received in a medullary canal of a femur. The femoral prosthesis further includes a neck that extends out with respect to the proximal core body end. The femoral prosthesis further includes a porous casing that encases at least a portion of the core body. The porous casing defines an inner casing surface that faces the core body and an outer casing surface opposite the inner casing surface. The inner surface of the porous casing extends along a central inner casing axis that is substantially coincident with the central core body axis. The outer surface of the porous casing extends along a central outer casing axis that intersects the central inner casing axis within an outer perimeter of the core body with respect to a side elevation view of the stem component that includes the proximal core body end, the distal core body end, the medial core body side, and the lateral core body side.

In another embodiment, a femoral prosthesis can include a core body and a casing that surrounds at least a portion of the core body. The casing can be additively manufactured to produce a plurality of femoral prostheses that include substantially identical core bodies, but also define at least one respective geometry that differs from the other of the femoral prostheses.

In one example, the femoral implant can include a core that includes the core body and a neck that extends out with respect to the core body at a fixed angle. The at least one respective geometry can include a selectable neck angle that is defined by a central neck axis and a central axis of an outer casing surface of the casing. Alternatively or additionally, the at least one geometry can include a neck offset measured from the casing to the neck along a direction substantially parallel to the central neck axis. Alternatively or additionally still, the at least one geometry can include a rotational position of the core body in the casing.

In another example, the casing can define an inner casing surface that faces the core and extends along a central inner casing axis. The core body can extend along a core body axis that is substantially coincident with the central inner casing axis. The outer casing surface can extend along a central outer casing axis that is angularly offset with respect to the central inner casing axis.

In another example, the casing can define a thickness that extends from the inner casing surface to the outer casing surface. The thickness can increase in a distal direction at one of a medial side of the casing and a lateral side of the casing, and can decrease in the distal direction at the other of the medial side of the casing and the lateral side of the casing.

In another embodiment, a femoral prosthesis includes an elongate core body that defines a medial core body side and a lateral core body side opposite the medial core body side substantially along a medial-lateral direction. The femoral prosthesis further includes a neck that extends out with respect to the elongate core body. The femoral prosthesis further includes a porous casing that encases at least a portion of the core body. The porous casing can define an inner casing surface that faces the core body and an outer casing surface opposite the inner casing surface. The porous casing can define an anterior casing surface and a posterior casing surface opposite the anterior casing surface substantially along an anterior-posterior direction. The medial core body side can define a first distance from the anterior side along the anterior-posterior direction and a second distance from the posterior side along the anterior-posterior direction that is different than the first distance.

In one example, the core body can be angulated such that the medial core body side defines a first distance from an anterior side of the casing along an anterior-posterior direction and a second distance from a posterior side of the casing along the anterior-posterior direction that is different than the first distance.

In another embodiment, a first femoral prosthesis and a second femoral prosthesis each define a medial side and a lateral side opposite the medial side along a medial-lateral direction, and an anterior side and a posterior side opposite the anterior side along an anterior-posterior direction. Each of the first and second femoral prostheses include a core having a core body elongate along a core body axis, the core body defining an outer core body surface. The core further has a neck that is monolithic with the core body, wherein the neck extends out with respect to the core body along a central neck axis. The core of the first femoral prosthesis is substantially identical to the core of the second femoral prosthesis. The first femoral prosthesis and the second femoral prosthesis each further include a porous casing that encases at least a portion of the core body. The porous casing defines an inner casing surface that extends along the outer core body surface, and an outer casing surface that is opposite the inner casing surface. The outer casing surface defines a central outer casing axis. Each of the first femoral prosthesis and the second femoral prosthesis includes a geometry that includes at least one of a selectable neck angle defined by the central neck axis and the central outer casing axis, a neck offset that extends from the neck to the casing along the central neck axis, and a rotational position of the core body relative to the outer casing surface about an axis that substantially perpendicular to each of the anterior-posterior direction and the medial-lateral direction. The geometry of the first femoral prosthesis is different than the geometry of the second femoral prosthesis.

In one example, the first femoral prosthesis defines a first selectable neck angle, and the second femoral prosthesis defines a second selectable neck angle different than the first selectable neck angle.

In another example, the first femoral prosthesis defines a first neck offset from the casing to the neck along the central neck axis, and the second femoral prosthesis defines a second neck offset from the casing to the neck along the central neck axis that is different than the first neck offset.

In another example, the core of second femoral prosthesis is rotated about the axis of rotation with respect to first femoral prosthesis.

In another example, the casing defines an anterior casing side and a posterior casing side opposite the anterior casing side along the anterior-posterior direction, and the core body defines a medial core body side and a lateral core body side opposite the medial core body side. The medial core body side of the second femoral prosthesis can be spaced further from the anterior casing side than the medial core body side of the first femoral prosthesis is spaced from the anterior casing side.

Each of the first femoral prosthesis and the second femoral prosthesis can further include a collar that extends at least medially out with respect to the outer core body surface.

BRIEF DESCRIPTION OF THE DRAWINGS

The detailed description particularly refers to the following figures, in which:

FIG. 7B is a sectional side elevation view of the femoral prosthesis illustrated in FIG. 7A, wherein the stem component defines a second selectable neck angle;

FIG. 7C is a sectional side elevation view of the femoral prosthesis illustrated in FIG. 7A, wherein the stem component defines a third selectable neck angle;

FIG. 9A is a sectional plan view of the femoral prosthesis illustrated in FIG. 1, wherein the stem component defines a first neck offset;

FIG. 9B is a sectional side elevation view of the femoral prosthesis illustrated in FIG. 9A, but shown wherein the stem component defines a second neck offset.

DETAILED DESCRIPTION

Figure 1:
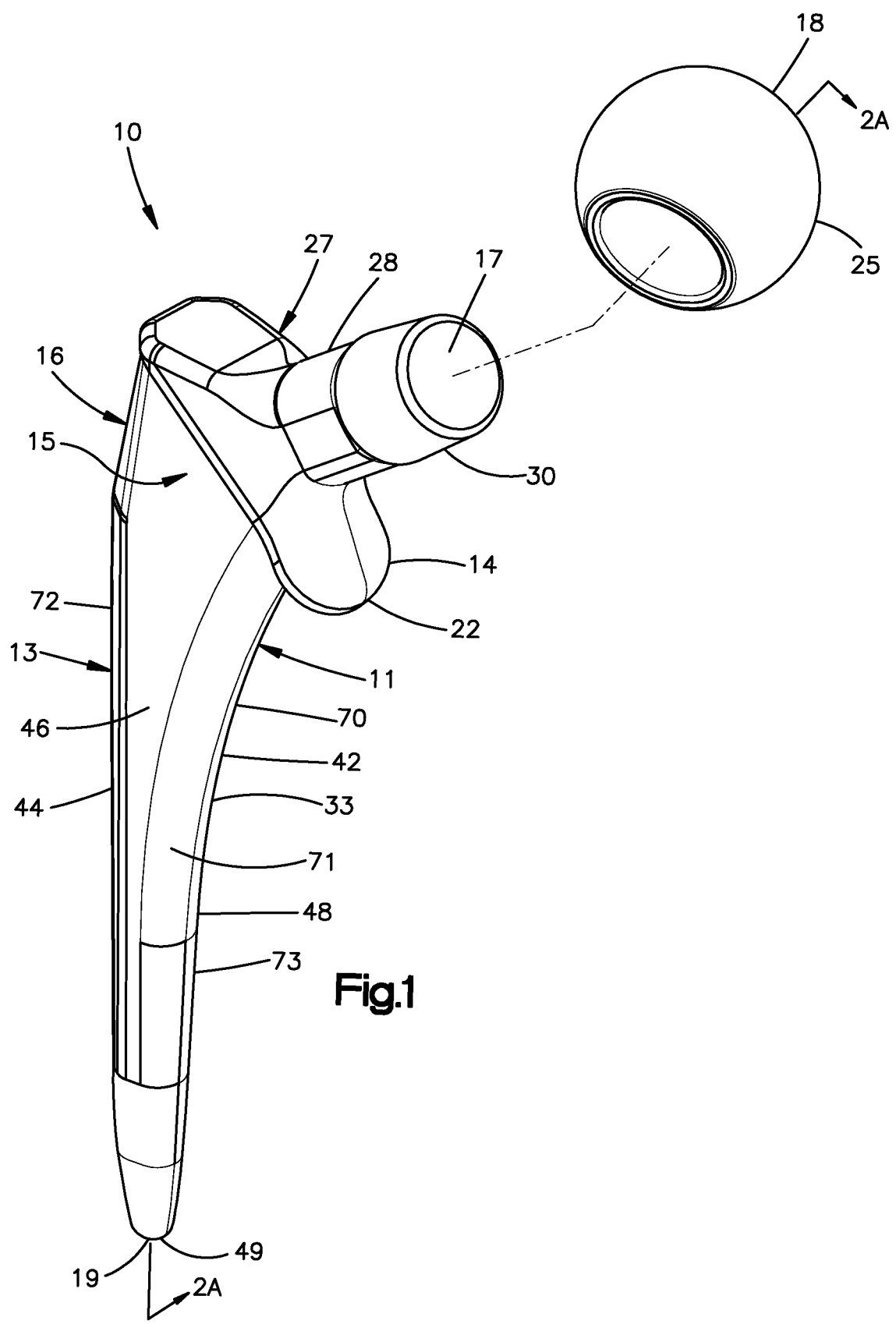
FIG. 1 is an exploded perspective view of a femoral prosthesis

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims. Further, the term "at least one" stated structure as used herein can refer to either or both of a single one of the stated structure and a plurality of the stated structure.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 2A:
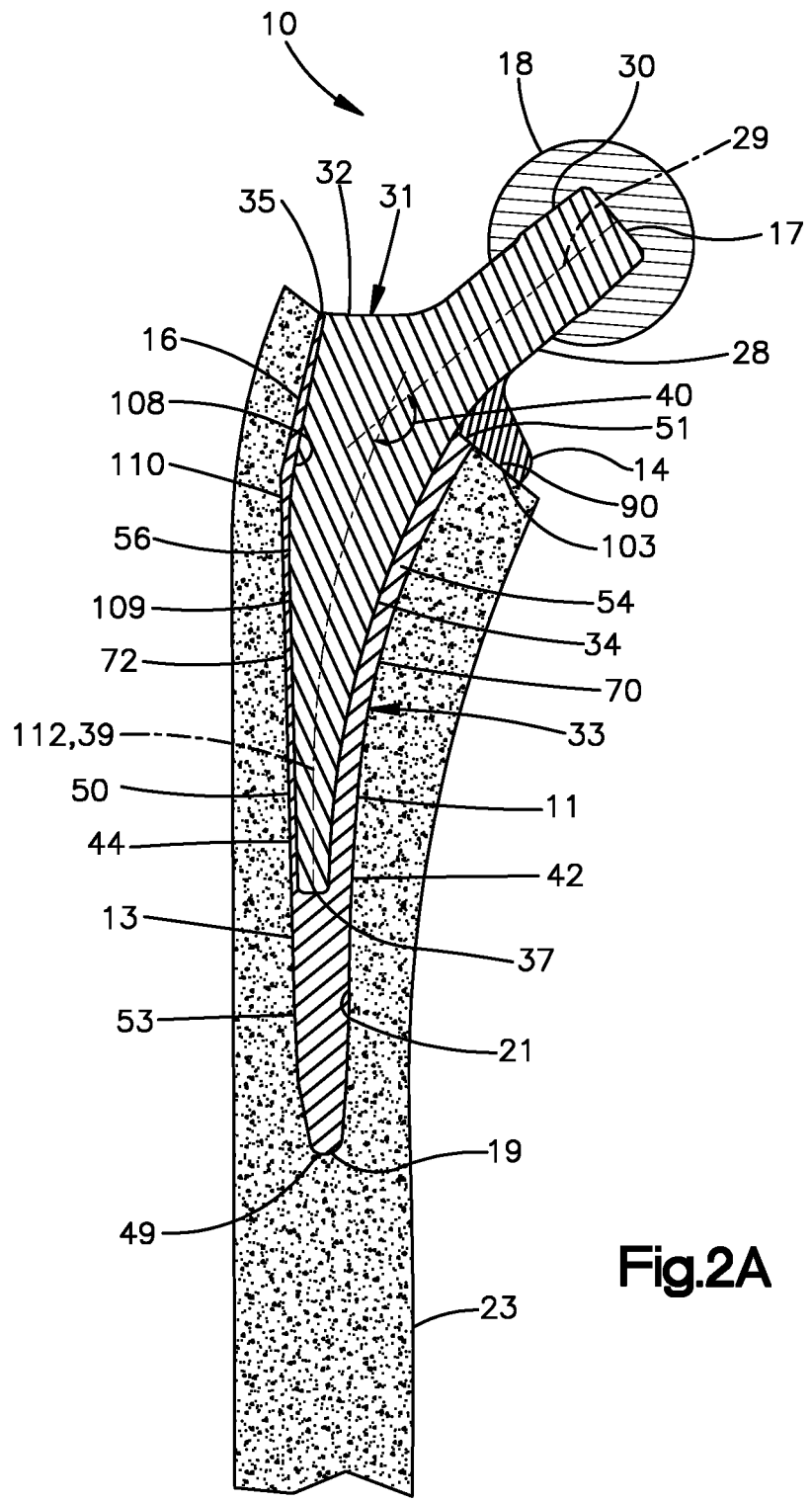
FIG. 2A is a sectional elevation view of the femoral prosthesis illustrated in FIG. 1, taken along line 2A-2A.

Referring to FIGS. 1-2A, a femoral prosthesis 10 of a hip prosthesis includes a femoral stem component 16 that is configured to be implanted into the medullary canal 21 of a patient's femur 23. The femoral prosthesis 10 can further include a head component 18 that is configured to attach to the femoral stem component 16. The head component 18 can define an outer articulation surface 25 that is configured to articulate along a complementary bearing surface of an acetabular prosthetic component that is implanted in the patient's acetabulum. In one example, the outer articulation surface 25 can be three-dimensionally curved. For instance, the outer surface can be substantially spherically shaped. An acetabular prosthetic component generally includes an outer shell configured to engage the acetabulum of the patient and an inner bearing or liner coupled to the shell that is configured to engage the femoral head component 18 to form a ball and socket joint that approximates the natural hip joint.

The femoral prosthesis 10 can define a medial side 11 and a lateral side 13 opposite the medial side 11 along a medial-lateral direction. Thus, the femoral prosthesis 10, and the elements thereof, defines a medial direction that is oriented from the lateral side 13 to the medial side 11, and a lateral direction that is oriented from the medial side 11 to the lateral side 13. The femoral prosthesis can further include an anterior side 15 and a posterior side 27 opposite the anterior side 15 along an anterior-posterior direction that is substantially perpendicular to the medial-lateral direction. Thus, the femoral prosthesis 10, and the elements thereof, defines an anterior direction that is oriented from the posterior side 27 to the anterior side 15, and a posterior direction that is oriented from the anterior side 15 to the posterior side 27. The anterior and posterior sides 15 and 27 each extend from the medial side 11 to the lateral side 13. Similarly, the medial and lateral sides each extend from the anterior side 15 to the posterior side 27.

Unless otherwise indicated herein, the term "substantially," "approximately," and derivatives thereof, and words of similar import, when used to describe a size, shape, angle orientation, distance, spatial relationship, or other parameter includes the stated size, shape, angle, orientation, distance, spatial relationship, or other parameter, and can also include a range up to 10% more and up to 10% less than the stated parameter, including 5% more and 5% less, including 3% more and 3% less, including 1% more and 1% less. The term "substantially" in the context of substantially perpendicular axis includes perpendicular, and can also include up to +/−25 degrees from perpendicular. The term "substantially identical" and derivatives thereof as used herein refer to being designed to be identical in size and shape, and thus within manufacturing tolerances. Thus, the term "different" when used in connection with a comparison to different sizes, orientations, angles, shapes, or other value means that the compared values are different than each other by design, and thus outside of manufacturing tolerances.

The femoral prosthesis 10 can further include a collar 14 that extends medially outward from the femoral stem component 16. In other examples, the femoral stem component 16 can include the collar 14. In use, an orthopaedic surgeon may assemble a femoral prosthesis 10 using the various components before implanting the assembled femoral prosthesis 10 in the patient's femur 23. For example, in some patients, the femoral prosthesis 10 may include only the stem component 16 and the femoral head component 18. For other patients, the orthopaedic surgeon may couple one of the collar 14 to the stem component 16 to address specific additional needs of a patient.

The stem component 16 defines a medial side 42 and a lateral side 44 opposite the medial side 42 substantially along a medial-lateral direction. The medial and lateral sides 42 and 44 of the stem component 16, respectively, define respective portions of the medial and lateral sides 11 and 13, respectively, of the femoral prosthesis. The stem component 16 further defines an anterior side 46 and a posterior side 48 opposite the anterior side 46 substantially along an anterior-posterior direction. The anterior and posterior sides 46 and 46, respectively, of the stem component 16 define a portion of the anterior and posterior sides 15 and 27, respectively, of the femoral prosthesis 10. The elements of the stem component 16 described below can similarly define respective anterior and posterior sides. The medial side 42 and the lateral side 44 are spaced from each other a first distance, and the anterior side 46 and the posterior side 48 are spaced from each other a second distance that is less than the first distance.

The stem component 16 can include an elongate core body 34 and a neck 28 that extends out with respect to the elongate core body 34. For instance, the neck 28 can extend out from the core body 34. The core body 34 can thus extend distally from the neck 28. Alternatively, the stem component 16 can further include a shoulder 32 that is disposed between the core body 34 and the neck 28. Thus, the neck 28 can extend out from the shoulder 32 that, in turn, extends out from the core body 34. Further, the core body 34 can extend distally from the shoulder 32. Either way, it can be said that the core body 34 extends distally with respect to the neck 28. The core body 34 is configured to be received in the medullary canal 21 of the patient's femur 23. The neck 28 can extend out with respect to the core body 34 at a fixed neck angle 40.

The stem component 16 can further include a trunnion 30 that extends superiorly and medially from the neck 28. The stem component 16 can define a proximal end 17. The proximal end 17 can be defined by the trunnion 30 in some examples. The trunnion 30 is configured to attach to the femoral stem component 16. The trunnion 30 is shaped to be received in a matching bore (not shown) of the femoral head component 18. The bore and the trunnion 30 can have matching tapers such that the femoral head component 18 may be secured to the stem component 16 via a Morse taper locking connection. In other embodiments, the trunnion 30 and the surface lining the bore of the femoral head component 18 may be threaded.

The core body 34 can extend distally to a distal core body end 37 of the core body 34. The stem component 16 can further include a casing 33 that encases at least a portion of an entire length of the core body 34. In the illustrative embodiment, the core body 34 and the surrounding casing 33 are shaped to be received in the medullary canal 21 patient's femur 23 via a press-fit to secure the stem component 16, to the patient's femur 23. In other embodiments, the core body 34 and the surrounding casing 33 may be secured to the femur 23 via other attachment means such as, for example, bone cement. The stem component 16 can define a distal end 19 that is opposite the proximal end 17. The distal end 19 of the stem component 16 can be defined by the casing 33 in some examples. In other examples, for instance whereby the casing does not extend along the entire length of the core body 34, the distal end of the stem component 16 can be defined by the casing 33. Thus, the stem component 16, the core body 34, and the casing 33 can define a proximal direction from the distal end 19 to the proximal end 17. Conversely, the stem component 16, the core body 34, and the casing 33 can define a distal direction from the proximal end 17 to the distal end 19.

Figure 3:
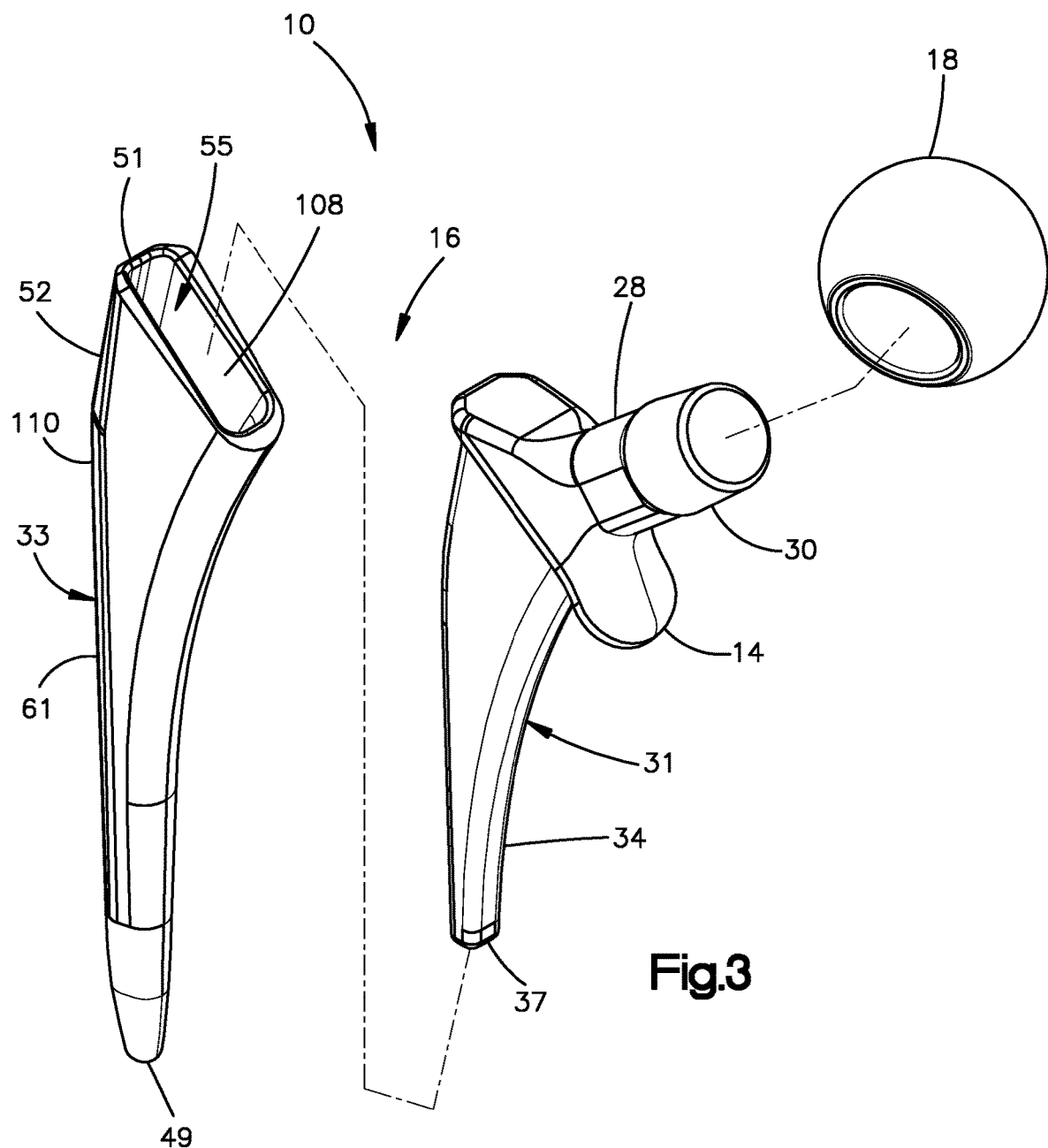
FIG. 3 is an exploded perspective view of a femoral prosthesis similar to the femoral prosthesis illustrated in FIG. 1.

As will be described in more detail below, the casing 33 extends over at least a portion of the core body 34. Thus, the casing 33 defines an inner casing surface 108 that faces an outer core body surface 109 of the core body 34, the casing 33, and an outer casing surface 110 opposite the inner casing surface 108. The casing 33 can be additively manufactured so as to encase the core body 34. For instance, the casing 33 can be additively manufactured onto the core body 34 so as to define a coating having an inner casing surface 108 that extends along the outer core body surface 109. Accordingly, the inner casing surface 108 can be coated onto the outer core body surface 109 after the casing has been additively manufactured onto the core body 34. Thus, the inner casing surface 108 can face the outer core body surface 109. Alternatively, as illustrated in FIG. 3, the casing 33 can be additively manufactured as a separate component 61 that is sized and configured to receive the core body 34. Thus, the casing 33 of the separate component 61 defines the inner casing surface 108 prior to attaching the casing 33 to the core body 34. The inner casing surface 108 of the casing 33 of the separate component 61 faces the core body 34 when the casing 33 receives the core body 34. Whether the casing 108 is additively manufactured onto the core body 34 or additively manufactured as the separate component 61, it can be said that the casing 33 encases at least a portion of the core body 34. The neck 28 can extend out with respect to the elongate core body 34. For instance, the neck 28 can extend out from the core body 34. Alternatively, the elongate body 34 can include the shoulder 32 that extends from the inner core body 34, such that the neck extends out from the shoulder 32.

Referring again to FIGS. 1-2B, the core body 34 can define a proximal core body end 35 and a distal core body end 37 opposite the proximal core body end 35. The proximal core body end 35 can be disposed at an interface between the core body 34 and the shoulder 32. Alternatively, in instances whereby the stem component 16 does not include the shoulder, the proximal core body end 35 can be disposed at an interface between the core body 34 and the neck 28. The core body 34 can define a distal core body end 37 opposite the proximal core body end 35 along a central core body axis 39. Thus, the elongate core body 34 can be elongate along the central core body axis 39 from a proximal core body end 35 to the distal core body end 37.

Referring again to FIGS. 1-2A, the distal core body end 37 can be spaced from the distal end 19 of the stem component in the proximal direction. For instance, the casing 33 can define a distal casing end 49 that is disposed distal of the distal core body end 37. The central core body axis 39 extends through the core body 34 from the proximal core body end 35 to the distal core body end 37. The central core body axis 39 extends centrally through the core body 34 with respect to a medial core body side 54 of the core body 34 and a lateral core body side 56 of the core body 34. The medial core body side 54 and the lateral core body side 56 can be opposite each other substantially along the medial-lateral direction. The medial core body side 54 and the lateral core body side 56 each extend from the proximal core body end 35 to the distal core body end 27. The medial core body side 54 and the lateral core body side 56 can define a portion of the medial side 42 and a lateral side 44 of the stem component 16. That is, the central core body axis 39 can extend centrally through the core body 34 with respect to a side elevation view of the core body 34 that includes the medial core body side 54 and the lateral core body side 56. Further, the central core body axis 39 can be centrally disposed with respect to the anterior and posterior sides, respectively, of the core body 34. The medial and lateral core body sides 54 and 56 can extend from the side and the posterior side of the core body 34.

Figure 8A:
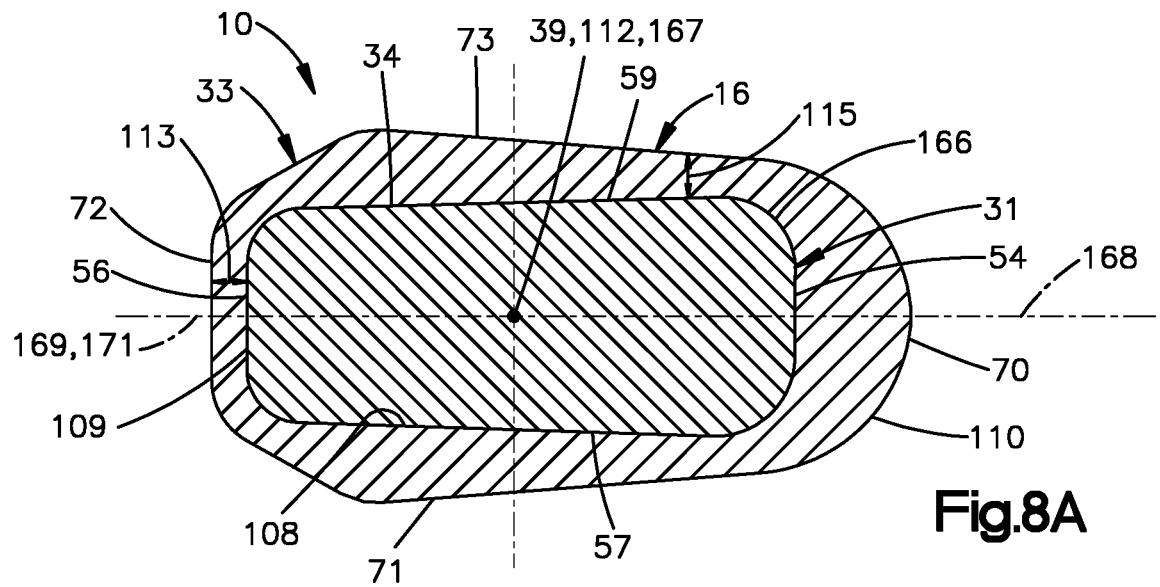
FIG. 8A is a sectional plan view of the femoral prosthesis illustrated in FIG. 1, wherein the stem component defines a first rotational position.
Figure 8B:
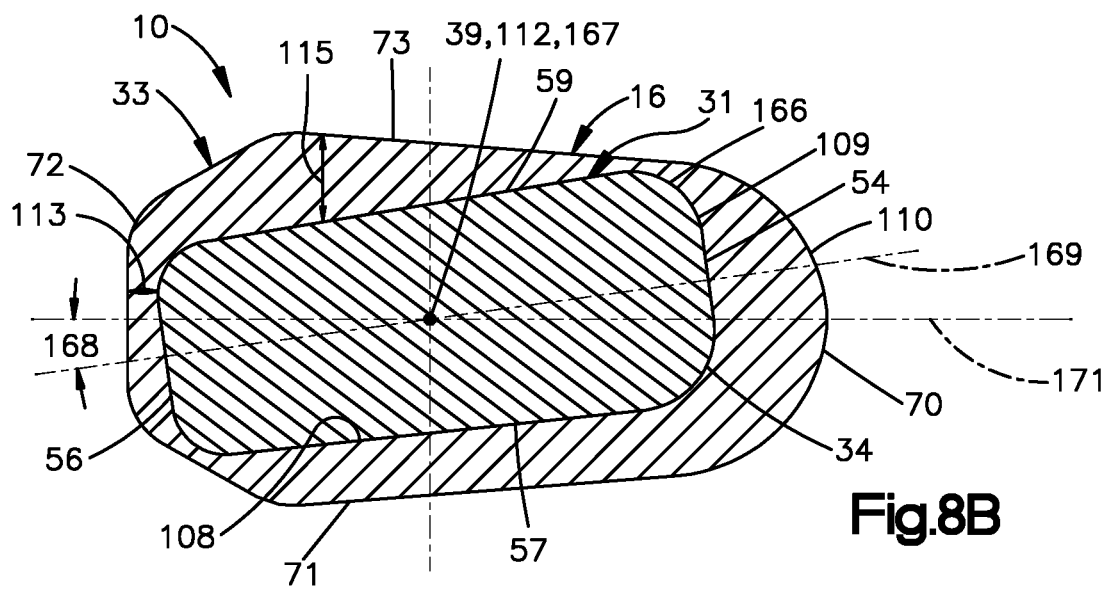
FIG. 8B is a sectional side elevation view of the femoral prosthesis illustrated in FIG. 8A, but shown wherein the stem component defines a second rotational position.
Figure 8C:
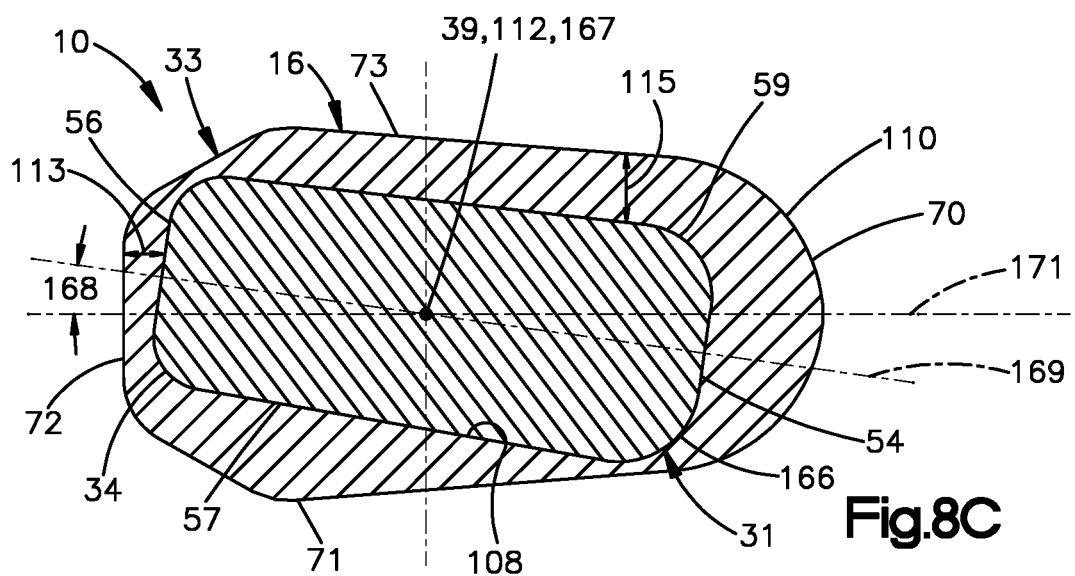
FIG. 8C is a sectional side elevation view of the femoral prosthesis illustrated in FIG. 8B, but shown wherein the stem component defines a third rotational position.

The core body 34 can further include an anterior core body side 57 and a posterior core body side 59 (see FIGS. 8A-8C). The anterior core body side 57 and the posterior core body side 59 can be opposite each other substantially along the anterior-posterior direction that is substantially perpendicular to the medial-lateral direction. The anterior core body side 57 and the posterior core body side 59 can define respective portions of the anterior side 46 and a posterior side 48 of the stem component 16, for instance at locations of the core body 34 that protrude from the casing 33. In one example, such locations can be at a superior end of the core body 34 that defines the proximal core body end 35. The anterior core body side 57 and the posterior core body side 59 can extend from the medial core body side 54 to the lateral core body side 56.

The central core body axis 39 can define any suitable shape depending on the design of the core body 34. For instance, the central core body axis 39 can be curved in one example. The central core body axis 39 can have a constant curvature. Alternatively, the central core body axis 39 can have curvatures that vary along its length. Alternatively, the central core body axis 39 can be straight and linear. Alternatively still, the central core body axis 39 can include a plurality of straight and linear segments that are angled with respect to each other. Alternatively still, the central core body axis 39 can include one or more straight and linear segments and one or more curved segments.

The casing 33 can also define a first or medial casing side 70 and a second or lateral casing side 72. The medial casing side 70 and the lateral casing side 72 are opposite each other along the medial-lateral direction. The medial and lateral casing sides 70 and 72, respectively, of the casing 33 can define at least a portion of the medial and lateral sides 42 and 44, respectively, of the stem component 16. The outer casing surface 110 at the medial and lateral casing sides 70 and 72 can taper toward each other as they extend distally.

The casing 33 can further include an anterior casing side 71 and a posterior casing side 73. The anterior casing side 71 and the posterior casing side 73 can be opposite each other substantially along the anterior-posterior direction that is substantially perpendicular to the medial-lateral direction. The anterior casing side 71 and the posterior casing side 73 can define respective portions of the anterior side 46 and a posterior side 48 of the stem component 16. The anterior casing side 71 and the posterior casing side 73 can extend from the medial casing side 70 to the lateral casing side 72.

In one example, the neck 28 can extend out from the core body 34 so as to define an inner core 31. For instance, the neck 28 can be monolithic with the core body 34 so as to define the inner core 31, which can be a single unitary structure. The inner core 31 can further include the trunnion 30. The trunnion 30 can be monolithic with the neck 28 and the core body 34. The inner core 31 can further include the shoulder 32. The shoulder 32 can be monolithic with the trunnion 30, the neck 28, and the core body 34 so as to define the inner core 31. Thus, the inner core 31 can be a single monolithic structure. Thus, it should be appreciated that the casing 33 can encapsulate at least a portion of an overall length of the core 31 as defined from the distal core body end 37 to the proximal end 17 of the trunnion 30. In one example, the inner core 31 can be made of any suitable biocompatible material, such as a metal. Further, the inner core 31, including the core body 34, the neck 28, the trunnion 30, and the shoulder 32, can be a forged metal. In one example, the inner core 31 can be made of stainless steel, cobalt chromium, titanium, tantalum, niobium, or alloys thereof. It is recognized, of course, that the inner core 31 can be made of any suitable alternative material, and fabricated using any suitable fabrication method as desired.

Figure 2B:
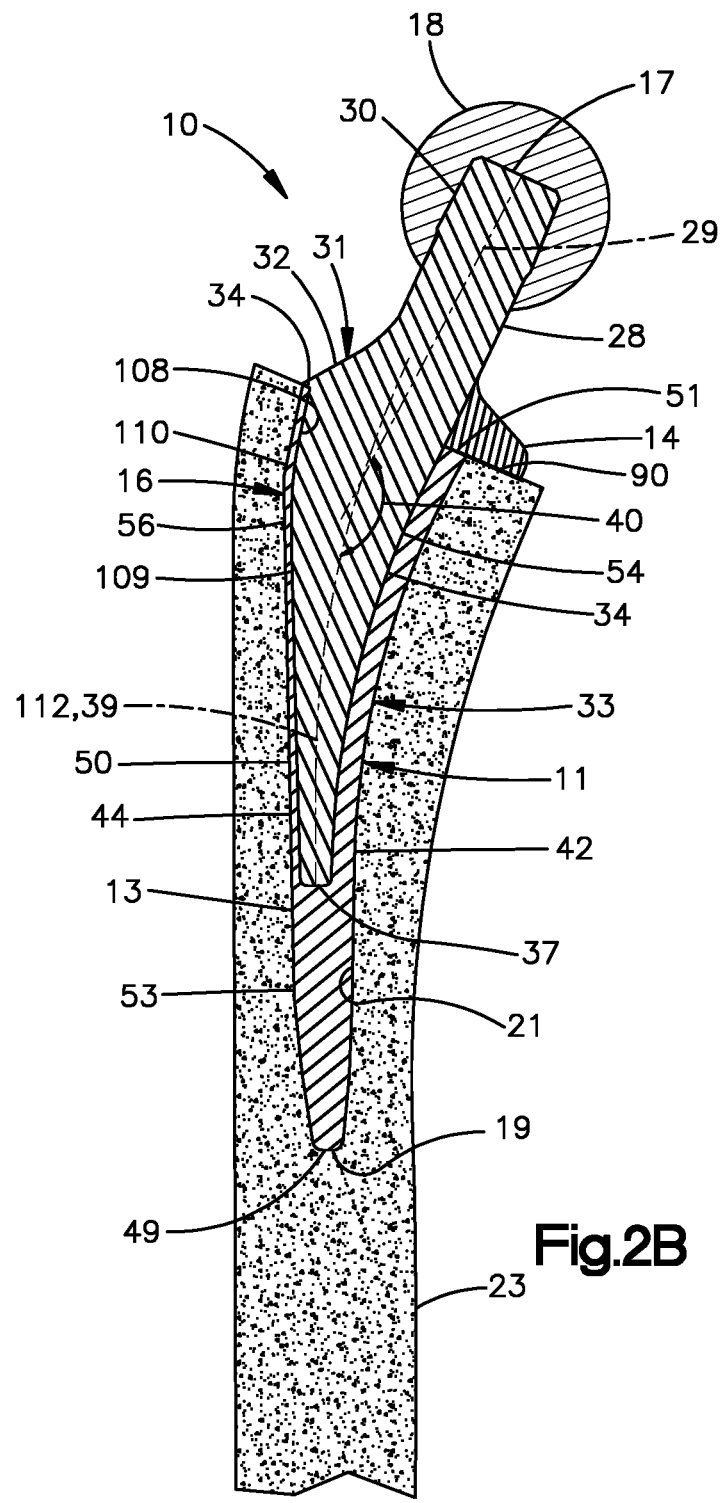
FIG. 2B is a sectional elevation view of a femoral prosthesis similar to the femoral prosthesis illustrated in FIG. 2A, but showing a different neck angle.

Referring now to FIGS. 2A-2B, the neck 28 can extend out with respect to the core body 34, and in particular the proximal core body end 35, along a central neck axis 29 that combines with the central core body axis 39 to define any desirable fixed neck angle 40 with respect to a side elevation view of the stem component 16 that includes the distal end 19 of the stem component 16, the proximal end 17 of the stem component 16, the medial side 42 of the stem component 16, and the lateral side 44 of the stem component 16. For instance, the neck 28 can extend out from the proximal core body end 35. Alternatively, the shoulder 32 can be disposed between the proximal core body end 35 and the neck 28. Thus, the neck 28 can extend out from the shoulder 32 that, in turn, extends out from the proximal core body end 35. Because the neck 28 and the core body 34 can be monolithic with each other, or otherwise secured to the core body 34, the neck angle 40 can be referred to as a fixed neck angle. That is, the fixed neck angle 40 cannot be altered without redesigning the core 31. In one example, the central neck axis 29 can be coplanar with the central core body axis 39 such that the axes 29 and 39 intersect each other so as to define the fixed neck angle 40. Alternatively, the central neck axis 29 and the central core body axis 39 can be non-coplanar with each other. Either way, the axes 29 and 39 intersect each other with respect to a side elevation view of the stem component 16 that includes the distal end 19 of the stem component 16, the proximal end 17 of the stem component 16, the medial side 42 of the stem component 16, and the lateral side 44 of the stem component 16. Further, because the inner casing surface 108 of the casing 33 can extend along the outer core body surface 109 of the core body 34, central neck axis 29 and the central inner casing axis 112 can define the angle 40. FIG. 2A illustrates the neck 28 extending out from the core body 34 at a first fixed neck angle 40. FIG. 2B illustrates the neck 28 extending out from the core body 34 at a second fixed neck angle 40 different than the first fixed neck angle 40.

The inner casing surface 108 can extend along a central inner casing axis 112. For instance, the inner casing surface 108 can be elongate along the central inner casing axis 112. The central inner casing axis 112 extends centrally through the casing 33 at a location centrally disposed with respect to the inner casing surface 108. For instance, the central inner casing axis 112 extends centrally through the casing 33 at a location centrally disposed with respect to the inner casing surface 108 at the medial casing side 70 and the inner casing surface 108 at the lateral casing side 72. That is, the central inner casing axis 112 extends through the casing 33 at a location centrally disposed with respect to the inner casing surface 108 along a sectional side elevation view of the casing 33 that includes the medial casing side 70 and the lateral casing side 72. Further, the central inner casing axis 112 can be centrally disposed with respect to the anterior casing side 71 and the and posterior casing side 73. Thus, it can be said that the inner casing surface 108 at the medial casing side 70 and the lateral casing side 72 combine to at least partially define the central inner casing axis 112. It can also be said that the inner casing surface 108 at the anterior casing side 71 and the posterior casing side 73 can also combine to partially define the central inner casing axis 112. Because the casing 33 can be coated onto the outer core body surface 109, the central inner casing axis 112 can be substantially coincident with the central core body axis 39. Thus, the fixed neck angle 40 can be defined by the central neck axis 29 and either or both of the central inner casing axis 112 and the central core body axis 39.

It is recognized that either or both of the central neck axis 29 and either or both of the central core body axis 39 and the central inner casing axis 112 can be curved where they intersect. Thus, the neck angle 40 can be measured by respective tangents to the central neck axis 29, the central core body axis 39, and the central inner casing axis 112 where they intersect, when the axes are curved where they intersect. In this regard, all angles disclosed herein defined by one or more curved axes can be measured by respective tangents of the one or more curved axes where the axes intersect. The central neck axis 29 can be coincident with a central axis of the trunnion axis. Alternatively, the trunnion 30 can be oriented such that the central axis of the trunnion is angularly offset with respect to the central neck axis 29.

As described above, the core body 34 extends along an overall length from the proximal core body end 35 to the distal core body end 37. The casing 33 can encase at least a portion of the overall length of the core body 34 up to an entirety of the overall length of the core body 34 from the proximal core body end 35 to the distal core body end 37. In particular, the casing 33 can surround the core body 34 along a plane that is oriented perpendicular to the central core body axis 39. Further, in some examples, the casing 33 can encapsulate the distal core body end 37. Thus, the distal casing end 49 can be disposed distal of the distal core body end 37. Further, the distal end 19 of the stem component 16 can be defined by the distal casing end 49. Alternatively, the casing 33 can terminate proximal of the distal core body end 37, such that the distal casing end 49 is spaced from the distal core body end 37 in the proximal direction. The casing 33 can further define a proximal casing end 51 opposite the distal casing end 49. The proximal casing end 51 can terminate at the shoulder 32 in some examples. Thus, the casing 33 can extend in the distal direction from the shoulder 32 to the distal casing end 49. In the event that the inner core 31 does not include the shoulder 32, the casing 33 can extend in the distal direction from the neck 28 to the distal casing end 49. In other examples, the casing 33 can extend to a location proximal of the neck 28. For instance, the casing 33 can encapsulate an entirety of the core 31. Thus, in this example, the proximal casing end 51 can define the proximal end 17 of the stem component 16.

As described above, the casing 33 can be additively manufactured. In one example, the casing 33 can be made of a porous material 53 as described in U.S. patent application Ser. No. 16/365,557 filed Mar. 26, 2019, the disclosure of which is hereby incorporated by reference as if set forth in its entirety herein. Because the casing 33 is made of the porous material 53, the casing 33 can be referred to as a porous casing. Additive manufacturing processes can include, by way of example, powder bed fusion printing, such as melting and sintering, cold spray 3D printing, wire feed 3D printing, fused deposition 3D printing, extrusion 3D printing, liquid metal 3D printing, stereolithography 3D printing, binder jetting 3D printing, material jetting 3D printing, and the like.

Figure 4:
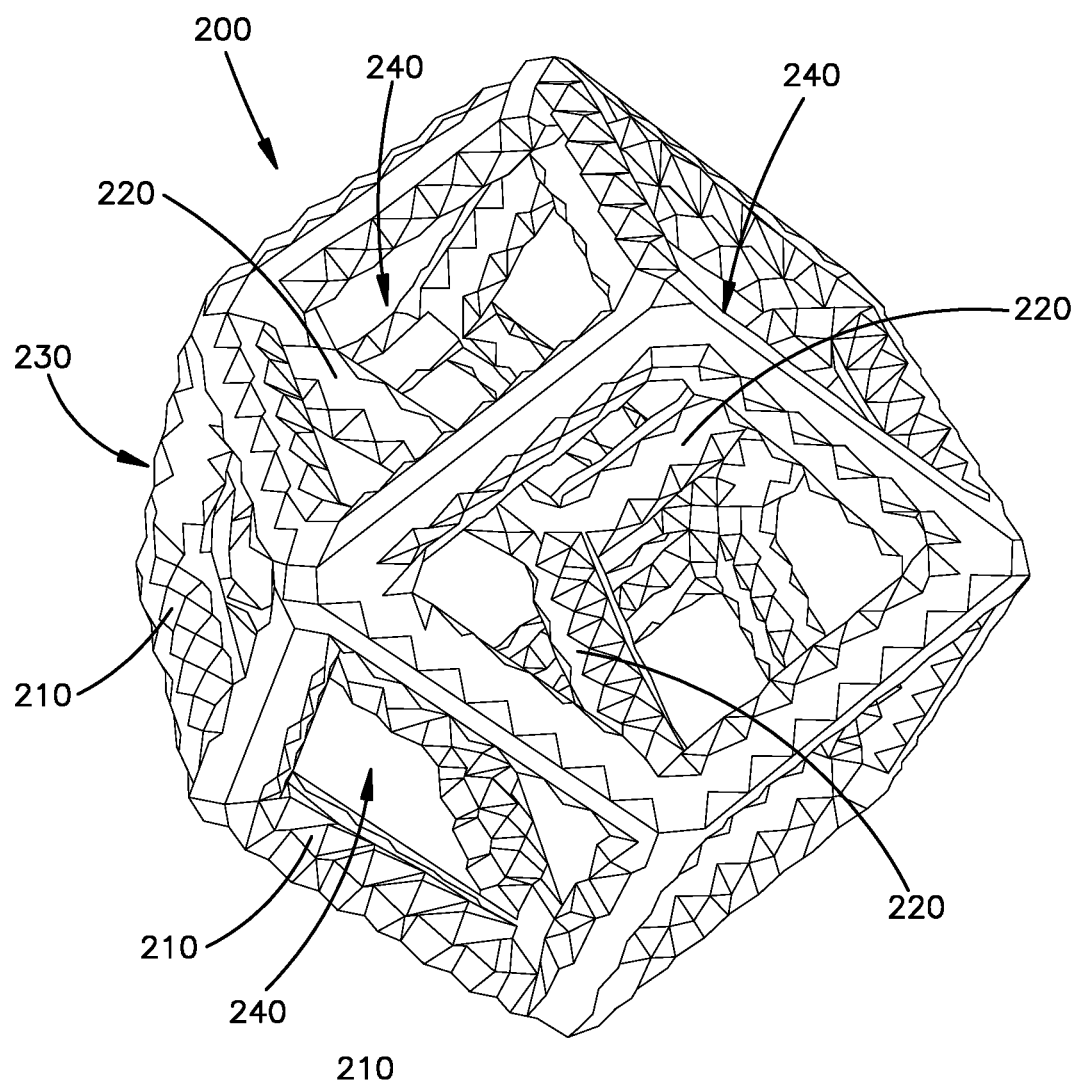
FIG. 4 is a perspective view of a portion of a porous casing of the femoral prosthesis illustrated in FIGS. 1 and 3.

In one example, referring to FIG. 4, the porous material 53 of the casing 33 can be defined by a porous three-dimensional structure that can comprise a plurality of connected unit cells. Each unit cell can define a unit cell structure 200 that includes a plurality of lattice struts 210 and a plurality of internal structs 220 so as to define a first geometric structure 230 and a plurality of second geometric structures 240 that are disposed within the first geometric structure 230. In one example, the first geometric structure 230 can include the plurality of lattice struts 210. The lattice struts 210 cooperate to define the first geometry. Each of the plurality of second geometric structures 240 can define an internal volume that is substantially equal to the internal volumes of the other second geometric structures 240. Each second geometric structure 240 can be formed by a plurality of the internal struts 220 and a plurality of the lattice struts 210. In one example, the first geometric structure can be a rhombic dodecahedron, and the second geometric structure can be a rhombic trigonal trapezohedron. It should be appreciated, of course, that the first and second geometric structures can vary as desired. Further, it should be appreciated that the unit cells that make up the casing 33 can have any suitable alternative geometry as desired.

The porous material 53 can be a metal powder that can be used to form the casing 33. In one example, the metal powders can include, but are not limited to, titanium, titanium alloys, stainless steel, cobalt chrome alloys, tantalum, or niobium powders. As illustrated in FIGS. 2A-2B, the porous material 53 can have a porosity suitable to facilitate bony ingrowth into the femoral prosthesis 10 when the core 31 is disposed in the medullary canal 21, but can be sufficiently solid such that the femoral prosthesis 10 has a desired rigidity. It is appreciated, of course, that the porous material can be any suitable alternative biomedical material. For instance, the porous material 53 can be a powder that can be used to form the casing 33. In one example, the powder can be a metallic powder. Alternatively, the powder can be a polymeric powder, such as pollyetheretherketone (PEEK). For instance, the PEEK can be a composite-reinforced PEEK. The composite has an elastic modulus of approximately 21.5 GPa and an ultimate tensile strength of approximately 223 MPa. Thus, the casing 33 has an elastic modulus that is similar to that of a patient's femur. In other embodiments, the casing 33 can be formed of any suitable composite or polymeric material having a low elastic modulus, such as, for example, a glass-filled polymer such as glass-filled PEEK, a non-reinforced polymer such as neat PEEK, or any other suitable reinforced or non-reinforced polymer.

In one example, the casing 33 can be additively manufactured directly onto at least a portion of the core body 34 so as to define a porous coating 50 that surrounds the core body 34. Alternatively, as illustrated in FIG. 3, the casing 33 can be manufactured as a separate sleeve 52 that can be coupled to the inner core 31. In particular, the sleeve 52 can define an internal void 55 that receives the inner core 31, such that the casing 33 surrounds at least a portion of the core 31 in the manner described herein. The sleeve 52 can be adhesively attached to the inner core 31 or attached using any suitable mechanical device such as one or more screws or other fasteners.

Figure 5:
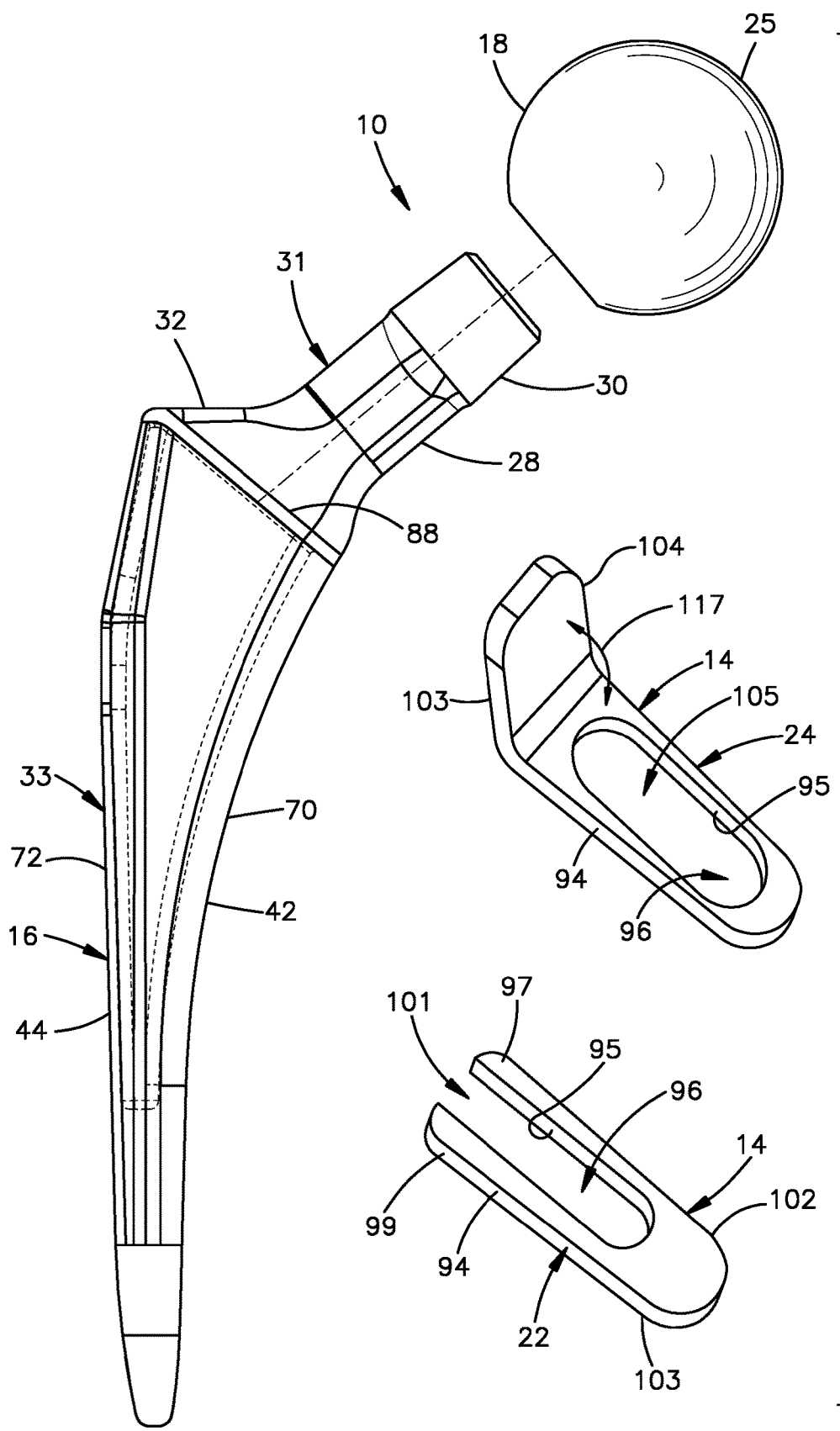
FIG. 5 is an exploded perspective view of the femoral prosthesis illustrated in FIG. 1, further showing a plurality of collars.
Figure 6A:
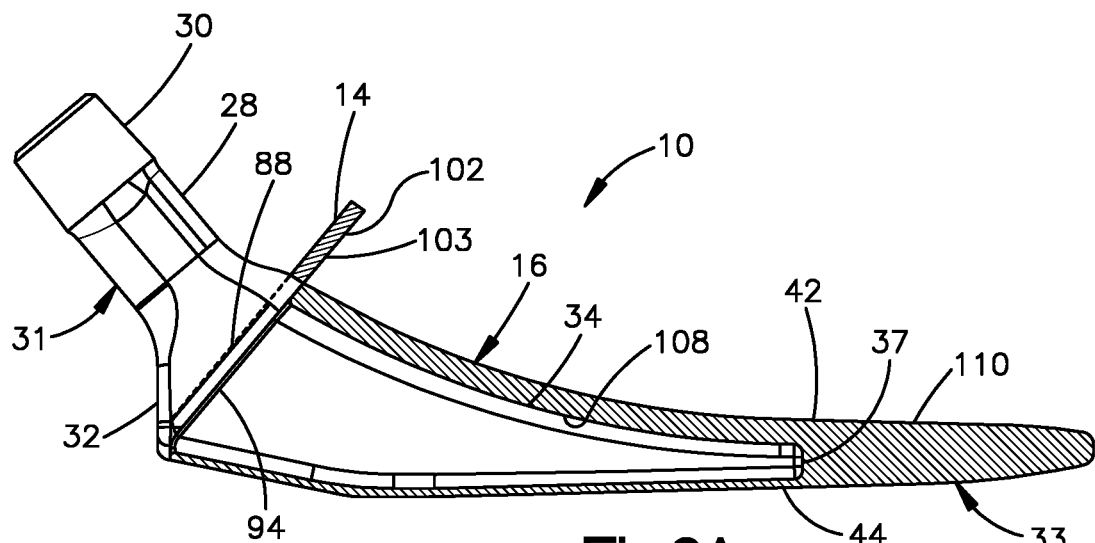
FIG. 6A is a sectional elevation view of the femoral prosthesis illustrated in FIG. 1, showing one of the collars of FIG. 5 attached to the core.
Figure 6B:
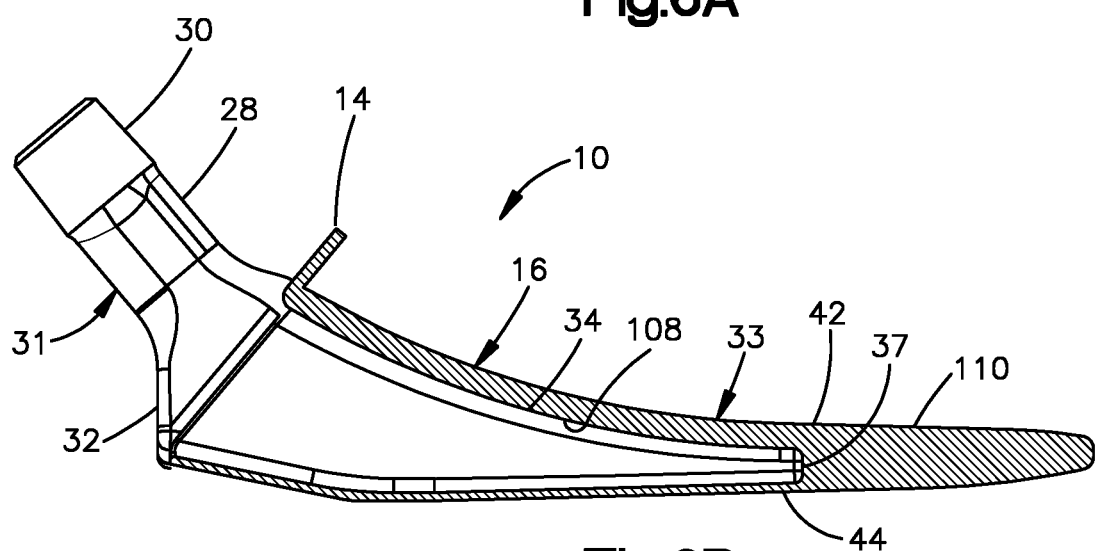
FIG. 6B is a sectional elevation view of the femoral prosthesis illustrated in FIG. 1, showing a collar monolithic with the casing.
Figure 6C:
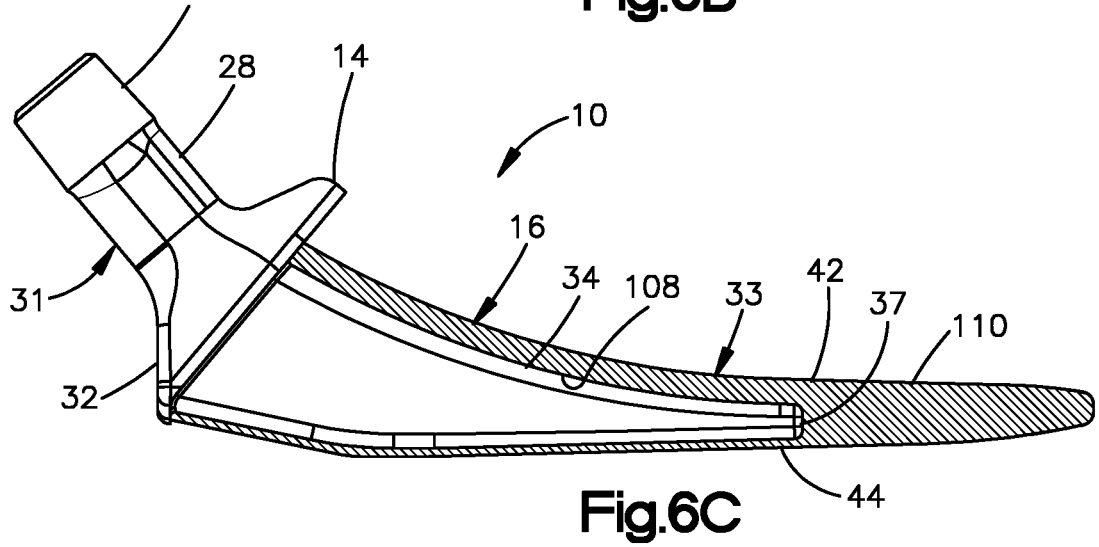
FIG. 6C is a sectional elevation view of the femoral prosthesis illustrated in FIG. 1, showing a collar monolithic with the core.

Referring now to FIG. 5-6C generally, and as described above, the femoral prosthesis 10 can further include one of a plurality of collars 14. For instance, referring now to FIGS. 5 and 6A, the collars 14 can include a stabilizing collar 22 and a trochanter collar 24 that may be selectively secured to the femoral stem component 16. As described in greater detail below, each collar 14 is configured to be coupled to the stem component 16 in a fixed, immoveable position relative to the stem component 16. Alternatively, the collar 14, including one of the stabilizing collar 22 and the trochanter collar 24, can be monolithic with the inner core 31 or the casing 33. When the femoral prosthesis 10 is implanted in the patient's femur 23, the collar 14 is configured to engage the patient's femur 23 to provide additional stability for the femoral prosthesis 10. It should be appreciated that in other embodiments the plurality of collars 14 of the femoral prosthesis 10 may include additional collar configurations, including collars of different sizes and shapes.

In an illustrative embodiment, each collar 14 can formed from a resorbable material that may be assimilated into the body over time. In the one example, each collar 14 can be made of a rigid polymer such as polyetheretherketone (PEEK). The collar 14 can be additively manufactured as described above with respect to FIG. 4. Thus, the collar 14 can be a porous PEEK. As a result, each collar 14 is capable of providing more stability than a stem component 16 alone and is easier to manipulate in the event that a revision hip replacement is necessary. In other embodiments, one or more of the collars 14 may be formed from a medical-grade metallic material such as stainless steel, cobalt chrome, or titanium, although other metals or alloys may be used. In this regard, the collar 14 can be made from the same material as the casing 33. Thus, the collar 14 can be referred to as a porous collar. Further, the collar 14 can be additively manufactured as described herein with respect to the casing 33.

Referring to FIG. 5-6A, the shoulder 32 can be configured to be secured to one of the collars 14. For instance, the stem component 16 includes a groove 88 that is formed at least in the anterior side and the posterior side of the stem component 16. The groove 88 can be defined at the shoulder 32 or any suitable alternative location of the stem component 16. The groove 88 can be sized to receive portions of the collar 14 to secure the collar 14 to the stem component 16 via a press-fit or other suitable mechanical connection.

The collar 14 can include one of a stabilizing collar 22 and a trochanter collar 24 in one example. Each of the collars 22 and 24 is configured to engage a surgically prepared proximal surface 90 of the patient's femur 23 (see FIGS. 2A-2B) when the femoral prosthesis 10 is positioned in the patient's femur 23. In other embodiments, however, the trochanter collar 24 may not engage the surgically prepared proximal surface of the patient's femur 23 and may be configured to only engage a portion of the patient's trochanter.

For instance, each of the collars 22 and 24 can include a base 94 that is configured to attach to the stem component 16. The base 94 is configured to be received in the groove 88. The base 94 defines an aperture 96 that is configured to receive the stem component 16, such that at least one inner wall 95 of the base 94 that at least partially defines the aperture 96 is received in the groove 88 of the stem component 16.

The stabilizing collar 22 can define an opening formed at a lateral end of its base 94 so as to define a pair of arms 97 and 99 that are spaced from each other. Thus, the arms 97 and 99 can combine to define the at least one inner wall 95 that is received in the groove 88 to couple the stabilizing collar 22 to the stem component 16. The aperture 96 defines an open-ended slot 101 between the arms 97 and 99 that is configured to receive the stem component 16 as the stabilizing collar 22 is moved along the lateral direction so as to receive the stem component 16 in the slot 101.

The illustrative aperture 96 of the trochanter collar 24 can define a closed through-hole 105 that extends through its base 94. The through-hole 105 can be defined by the inner wall 95 of the trochanter collar 24. The through hole 105 can receive the stem component 16 along one of the proximal direction and the distal direction. The inner wall 95 can ride along the stem component 16 until the inner wall 95 is resiliently forced into the groove 88 of the stem component 16, thereby securing the trochanter collar 24 to the stem component 16.

The stabilizing collar 22 can further include an abutment member 102 that extends medially out from the base 94. Thus, the abutment member 102 can further extend out with respect to the neck 28 in any suitable predetermined direction. For instance, the abutment member 102 can extend medially out with respect to the neck 28. The abutment member 102 can be substantially coplanar with the base 94. The abutment member 102 can define an inferior surface 103 that is configured to abut the surgically prepared proximal surface 90 of the patient's femur 23 during use.

The trochanter collar 24 can further include an abutment member 104 that extends out from the base 94. For instance, the abutment member 104 can extend away from the base 94 along any suitable predetermined direction and cooperates with the base 94 so as to define a non-orthogonal angle 117. When the trochanter collar 24 is coupled to the stem component 16, the abutment member 104 extends medially and superiorly out with respect to the neck 28. The abutment member 104 of the trochanter collar 24 can define an inferior surface 103 that is configured to abut the surgically prepared proximal surface 90 of the patient's femur 23 during use. It should be appreciated that the aperture 96 of the stabilizing collar 22 can alternatively define a through-hole, and the aperture 96 of the trochanter collar 24 can alternatively define an open-ended slot.

In still other examples, such as is shown in FIG. 6B, the collar 14 can be monolithic with one the casing 33. Alternatively still, as illustrated in FIG. 6C, the collar 14 can be monolithic with the inner core 31. Alternatively still, as illustrated in FIG. 9A, the femoral prosthesis 10 can be devoid of a collar.

As will now be described with reference to FIGS. 7A-9B, a plurality (i.e., greater than one) of different femoral prostheses 10, such as first and second femoral prostheses, can be fabricated from the same core 31. The femoral prostheses 10 can further be customized for different patients. For instance, the femoral prostheses can define at least one respective geometry that differs from the other of the femoral prostheses. The term "selectable" in connection with any of the geometries described herein indicate a geometry within a range of permissible geometries for the femoral prosthesis 10.

Figure 7A:
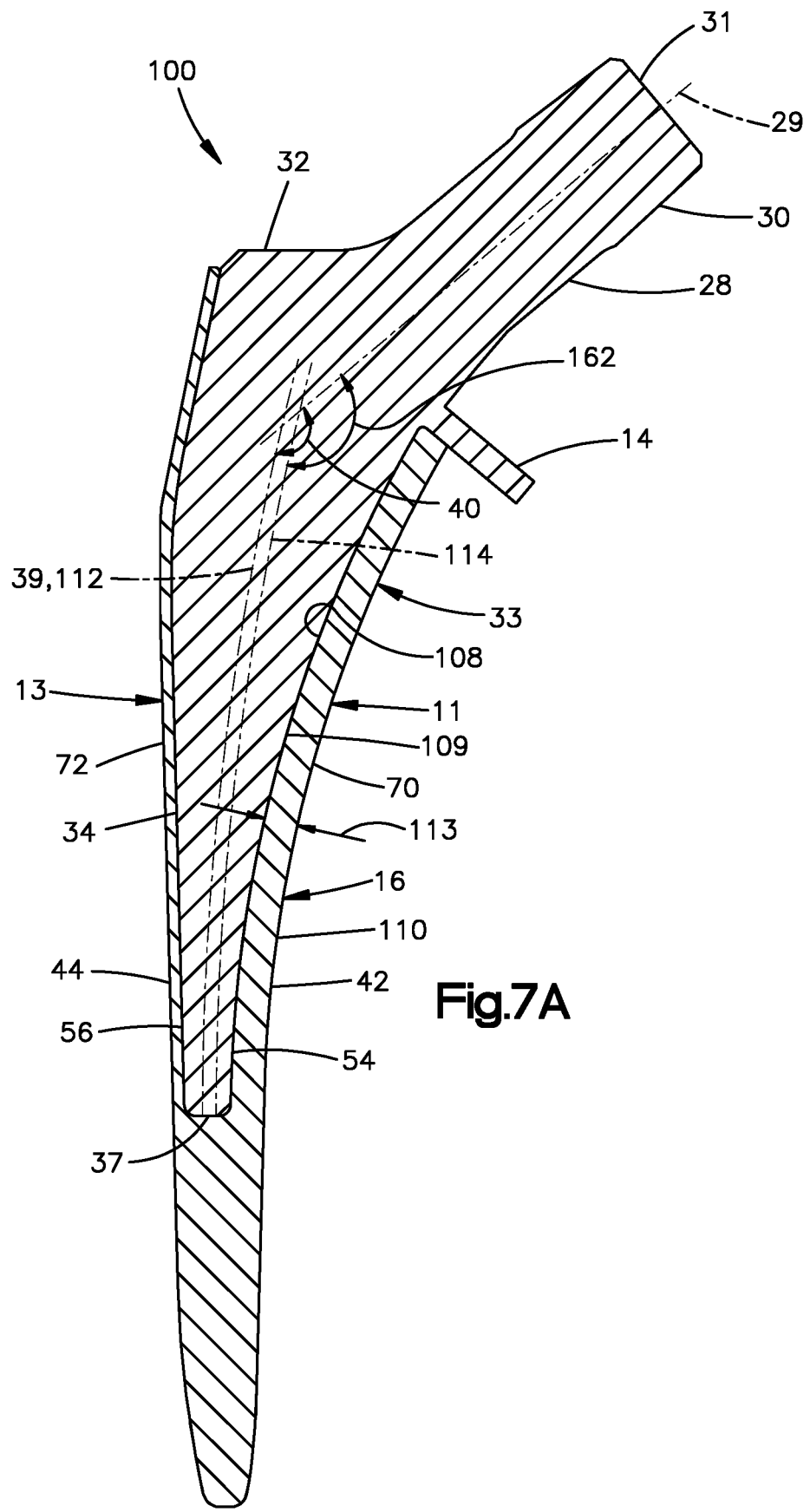
FIG. 7A is a sectional elevation view of the femoral prosthesis illustrated in FIG. 1, wherein the stem component defines a first neck angle.

As illustrated in FIGS. 7A-7C, the geometry can include a selectable neck angle 162. Thus, while the fixed neck angle 40 can be the same for the first and second femoral prosthesis 10, the selectable neck angle 162 of a first femoral prosthesis 10 can be different than the selectable neck angle 162 of a second femoral prosthesis 10. The selectable neck angle 162 can be different than the fixed neck angle.

Alternatively or additionally, referring to FIGS. 8A-8C, the geometry can include a rotational position 166 of the core body 34, and thus of the core 31. In particular, the inner core 31 can define a rotational position 166 relative to the outer casing surface 110 about an axis of rotation 167 that is oriented in a directed substantially perpendicular to each of the medial-lateral direction and the anterior-posterior direction. Accordingly, the rotational positions 166 can be defined in a plane that defined by the anterior-posterior direction and the medial-lateral direction. The first femoral prosthesis 10 can define a first rotational position 166, and the second femoral prosthesis 10 can define a second rotational position 166 that is different than the first rotational position 166.

Alternatively or additionally still, as illustrated in FIGS. 9A-9B, the geometry can include a neck offset 164. The neck offset 164 extends from the core 31 to the neck 28 substantially along the central neck axis 29. Thus, the first femoral prosthesis 10 can define a first neck offset 164, and the second femoral prosthesis 10 can define a second neck offset 164 that is different than the first neck offset. As will be described in more detail below, each of the selectable geometries can determine at least one or both of a position and an orientation of the neck 28 with respect to the outer casing surface 110.

Referring again to FIGS. 7A-9B generally, because the trunnion 30 can extend out from the neck 28 at a fixed position with respect to the neck 28, each of the selective geometries can further determine at least one or both of a position and orientation of the neck 28. Further still, because the head component 18 can be coupled to the trunnion 30, each of the selective geometries can further determine a position of the head component 18, and an orientation of the stem component 16 with respect to the head component 18 when the head component is received by the acetabular prothesis.

While first and second femoral prostheses 10 having a different one or more up to all of the selectable geometries are used as examples, but it should be appreciated that a plurality of femoral prostheses 10 can have one or more up to all different selectable geometries. Thus, it will be appreciated that a plurality of femoral prostheses 10 can be constructed using substantially identical inner cores 31 and can still be customized to better fit different specific patient anatomies. Thus, the femoral prosthesis 10 can be referred to as a patient specific femoral prosthesis. For large differences in patient anatomies greater than the difference attained by the selectable geometries described herein, as can occur in patients having significant age differences and gender differences, cores 31 of the type described herein can be produced having different sizes. However, the ability for the resulting femoral prosthesis to have at least one of the selectable geometries can result in a reduced number of stock keeping units (SKU) of the inner core 31 while allowing the femoral prosthesis 10 to accommodate a greater number of different patient anatomies that are currently accommodated using a greater number of SKUs than previously achieved. Further, in some examples, the outer casing surface 110 of the femoral prostheses 10 can have substantially the same size and substantially the same shape, such that femoral prostheses 10 having substantially the same size and shaped cores 31 can also define substantially the same size and shaped prosthesis 10.

It is recognized that each femoral prosthesis 10 can be fabricated for a specific patient anatomy. Thus, an orthopaedic implant system can include a plurality of femoral prostheses 10 that can be produced at different times, including a first femoral prosthesis and a second femoral prosthesis that is different than the first femoral prosthesis. The different prostheses 10 of the orthopedic implant system can be produced non-contemporaneously. For instance, different femoral prostheses 10 can be fabricated days, weeks, months or even years apart. Further, the femoral prostheses 10 of the orthopedic implant system can be packaged and delivered separately to different healthcare providers. Therefore, it is recognized that the plurality of femoral prostheses of the orthopedic implant system can be produced that are not provided in a single kit in some examples. In other examples, it is recognized that kits of the femoral prosthesis 10 described herein of the orthopedic implant system can be provided in a kit, such that a healthcare provider can have an inventory of the femoral prostheses 10 with one or more different selectable geometries among the plurality of selectable geometries described herein.

Referring now to FIGS. 7A-7C in particular, and as described above, the femoral prosthesis, can include a selectable neck angle 162 with respect to the casing 33. Thus, the neck 28 can extend out from the core body 34 both at the fixed neck angle 40 and at the selectable neck angle 162. As will now be described, the outer casing 33 can define the selectable neck angle 162. For instance, the outer casing 33 can be fabricated such that the core 31, and thus the neck 28, can define any suitable selectable orientation with respect to the outer casing.

The outer casing surface 110 of the casing 33 can extend along a central outer casing axis 114. For instance, the outer casing surface 110 can be elongate along the central outer casing axis 114. The central outer casing axis 114 extends centrally through the casing 33 at a location centrally disposed with respect to the outer casing surface 110. For instance, the central outer casing axis 114 can extend centrally through the casing 33 at a location centrally disposed with respect to the outer casing surface 110 at the medial casing side 70 and at the lateral casing side 72 of the casing 33. That is, the central outer casing axis 114 extends through the casing 33 at a location centrally disposed with respect to the outer casing surface 110 along a sectional side elevation view of the casing 33 that includes the medial casing side 70 and the lateral casing side 72. Thus, the central outer casing axis 114 can be centrally disposed with respect to the outer casing surface 114 at anterior casing side 71 and at the posterior casing side 73. Thus, it can be said that the outer casing surface 110 at the medial casing side 70 and at the lateral casing side 72 can at least partially define the central outer casing axis 114. It can also be said that the outer casing surface 114 at the anterior casing side 71 and the posterior casing side 73 can partially define the central outer casing axis 114.

The selectable neck angle 162 can be defined by the central neck axis 29 and the central outer casing axis 114. The central neck axis 29 can be coplanar with the central outer casing axis 114 such that the axes 29 and 114 intersect each other so as to define the selectable neck angle 162. Alternatively, the central neck axis 29 and the central outer casing axis 114 can be non-coplanar with each other. Either way, the axes 29 and 114 intersect each other with respect to a side elevation view of the stem component 16 that includes the distal end 19 of the stem component 16, the proximal end 17 of the stem component 16, the medial side 42 of the stem component 16, and the lateral side 44 of the stem component 16. It should thus be appreciated that the selectable neck angle 162 can be selected by determining an orientation of the core 31 with respect to the casing 33 about an axis that is oriented substantially along the anterior-posterior direction. It is further appreciated that axes 29 and 114 intersect each other inside an outer perimeter of the core body 34 with respect to the side elevation view of the stem component that includes the proximal core body end 35, the distal core body end 37, the medial core body side 54, and the lateral core body side 56. The outer perimeter of the core body 34 is defined by the proximal core body end 35, the distal core body end 37, the medial core body side 54, and the lateral core body side 56.

The femoral prosthesis 10 can be customized such that the neck 28 can define any suitable selectable neck angle 162 as desired. In particular, the casing 33 can be fabricated such that the core 31 defines any suitable predetermined selectable neck angle 162. For instance, as illustrated in FIG. 7A, the core body 34 can define a first selectable neck angle 162 within the casing 33. As illustrated in FIG. 7B, the core body 34 can define a second selectable neck angle 162 within the casing 33 that is different than the first selectable neck angle 162. As illustrated in FIG. 7C, the core body 34 can define a third selectable neck angle within the casing 33 that is different than each of the first and second selectable neck angles 162. The selectable neck angles 162 defined by the core body 34 within the casing 33 can be defined with respect to a sectional side elevation view that extends through both the core body 34 and the casing 33 and includes the medial core body side 54 and the lateral core body side 56. The sectional side elevation view can further include the medial casing side 70 and the lateral casing side 72.

In some examples, a permissible range of selectable neck angles 162 can be determined such that the at least a portion of the core body 34 is encapsulated by the casing at all of the selectable neck angles 162 within the permissible range of selectable neck angles 162. In one example, the permissible range of selectable neck angles 162 can be a substantially 30 degree range. That is, the central neck axis 29 can be angularly offset from the central outer casing axis from a position substantially 15 degrees offset from the central outer casing axis 114 in a negative direction to a position substantially 15 degrees offset from the central outer casing axis 114 in a positive direction. In this regard, it should be appreciated that the core body 34 can be sized substantially smaller than the footprint defined by the outer casing surface 110 along the medial-lateral direction to achieve a broader range of selectable neck angles 162. As the size of the core body 34 in the casing is increased with respect to the outer casing surface 110 along the medial-lateral direction, the range of selectable neck angles 162 can decrease.

It should be further appreciated that the selectable neck angle 162 in the range of selectable neck angles 162 can define a respective medial-lateral thickness profiles of the casing 33. In particular, the casing 33 can define a thickness 113 along the length of the core body 34 that is a function of the selectable neck angle 162 relative to the casing 33. The thickness 113 of the casing 33 can extend from the inner casing surface 108 to the outer casing surface 110 along the medial-lateral direction. As described above, the outer casing surface 110 can define at least a portion of the outer surface of the femoral prosthesis 10. Further, the outer casing surface 110 can be nonparallel with respect to the inner casing surface 108. It should be appreciated that as the orientation of the core body 34 is varies to correspondingly vary the selectable neck angle 162, the thickness of the casing 33 can similarly vary along the length of the casing 33. Further, the thickness 113 of the casing 33 can be maintained above a minimum thickness along an entirety of the medial and lateral casing sides 70 and 72, respectively. Alternatively, portions of the core body 34 can protrude through the casing 33. Accordingly, the outer casing surface 110 can be interrupted by core body 34, and thus can be discontinuous in some embodiments.

As illustrated in FIG. 7A, the core body 34 can be oriented with respect to the casing 33 such that the central core body axis 39 is oriented parallel with the central outer casing axis 114. In some examples, the central core body axis 39 can be coincident with the central outer casing axis 114. Further, the central inner casing axis 112 can be parallel to or coincident with the central core body axis 39. Further, the thickness 113 of the medial casing side 70 casing of the casing 33 can be substantially constant along an entirety of the length of the core body 34. Similarly, the thickness 113 of the lateral casing side 72 can be substantially constant along an entirety of the length of the core body 34. The thickness of the casing 33 at the medial casing side 70 can be greater than the thickness of the casing 33 at the lateral casing side 72.

As illustrated in FIG. 7B, casing 33 can be fabricated such that the central core body axis 39 is angularly offset with respect to the central outer casing axis 114. Thus, the central core body axis 39 can intersect the central outer casing axis 114 in the core body 34. Because the neck 28 extends out from the core body 34 at the fixed neck angle 40, the angular offset of the central core body axis 39 can further determine a first selectable neck angle 162. In one example, the central core body axis 39 can define a first angular offset with respect to the central outer casing axis 114. In particular, the central core body axis 39 can extend medially with respect to the central outer casing axis 114 as it extends in the distal direction. The first angular offset can be referred to as a negative angular offset in a negative direction. Further, the central inner casing axis 112 can be similarly angularly offset with respect to the central core body axis 39. For instance, the central inner casing axis 112 can define the first angular offset with respect to the central outer casing axis 114. The core body 34 of the femoral prosthesis illustrated in FIG. 7B can be substantially identical to the core body 34 of the femoral prosthesis illustrated in FIG. 7A.

As used herein, the term "angular offset" and derivatives thereof refers to a design in which two different axes are intended to be angularly offset, and thus outside of manufacturing tolerances. Thus, the term "angular offset" and derivatives thereof connotes that the angular offset is greater than manufacturing tolerances of two axes that are designed to be coincident with each other but might be offset due to manufacturing tolerances. In one example, the term "angular offset" can include an offset of at least approximately 1 degree, such as at least approximately 2 degrees.

Further, with continuing reference to FIG. 7B, the thickness 113 of the casing at the medial casing side 70 can decrease as the casing 33 extends in the distal direction. The thickness 113 of the casing at the lateral casing side 72 can increase as the casing extends in the distal direction. The terms "increase" and "decrease" and derivatives thereof when used in connection with dimensions or measurements connotes that the distance or measurement increases or decreases, respectively, an amount greater than manufacturing tolerances of a distance or measurement that is designed to be equal.

As illustrated in FIG. 7C, the core body 34 can be oriented such that the central core body axis 39 defines a second angular offset with respect to the central outer casing axis 114 different than the first angular offset, thereby determining a second selectable neck angle 162 different than the first selectable neck angle 162 of FIG. 7B. Thus, the central core body axis 39 can intersect the central outer casing axis 114 in the core body 34. In one example, the second angular offset can be opposite the first angular offset. In particular, the central core body axis 39 can extend laterally with respect to the central outer casing axis 114 as it extends in the distal direction. The second angular offset can be referred to as a positive angular offset in a positive direction. Further, the central inner casing axis 112 can be similarly angularly offset with respect to the central core body axis 39. For instance, the central inner casing axis 112 can define the second angular offset with respect to the central outer casing axis 114. Further, the thickness 113 of the medial casing side 70 can increase as the casing 33 extends in the distal direction. The thickness 113 of the lateral casing side 72 can decrease as the casing extends in the distal direction. As described above, the inner core 31 of the femoral prosthesis illustrated in FIG. 7C can be substantially identical to the inner core 31 of the femoral prosthesis illustrated in each of FIG. 7A and FIG. 7B.

Accordingly, it should be appreciated that a plurality of different femoral prostheses 10 can be manufactured having different selectable neck angles. For instance, the respective core bodies 34 of each of the plurality of cores 31 having substantially the same fixed neck angle can be encased by respective casings 33 that are fabricated about their respective outer core body surfaces 109, such that when the casings 33 are inserted into the medullary canal of a femoral bone at substantially the same relative orientation with respect to the bone, the respective necks having the same fixed neck angle will extend medially and superiorly at different angles with respect to the central axis of the femur. In one example, the casings 33 can have substantially identically sized and shaped outer casing surfaces 110.

The relative orientations of the central core body axis 39, the central inner casing axis 112, and the central outer casing axis 114 described above can be determined with respect to a sectional side elevation view of the stem component 16 that includes the medial casing side 70 and the lateral casing side 72. Further, an angle defined by the central outer casing axis 114 and either or both of the central core body axis 39 and the central inner casing axis 112 can be can be curved where they intersect when viewed along the sectional side elevation view. Thus, the angle can be measured by respective tangents of one or more up to all of the central outer casing axis 114 and either or both of the central core bony axis 39 and the central inner casing axis 112, when curved, where they intersect. It is further recognized that the central core body axis 39 can be angularly offset with respect to the central inner casing axis 112. For instance, it is recognized that portions of the inner casing surface 108 can be spaced from the outer core body surface 109, such as when the casing 33 is additively manufactured as a separate component 61 as shown in FIG. 3.

With continuing reference to FIGS. 7A-7C, it should be appreciated a method can be provided for fabricating the femoral prostheses 10 that each includes the core body 34 that is configured to be inserted into the medullary canal 21 of the femur 23. The femoral prostheses 10 can include substantially equally sized and shaped core bodies 34 having different orientations in the respective casings 33. A method of fabricating the femoral prosthesis 10 can include the step of applying the porous casing 33 onto the core body 34 so as to define the inner casing surface 108 that faces the core body 34 and the outer casing surface 110 opposite the inner casing surface 108, such that the central core body axis 39 of the core body 34 is angularly offset with respect to the central outer casing axis 114 defined by the outer casing surface 110. The angular offset between the central core body axis 39 and the central outer casing axis 114 similarly determines the selectable neck angle 162.

For instance, the first femoral prosthesis can include a first core body and a first neck that extends out with respect to the first core body at the fixed neck angle 40 and at a first selectable neck angle 162. The second femoral prosthesis can include includes a second core body and a second neck that extends out with respect to the second core body at the fixed neck angle 40 and at a second selectable neck angle 162 different than the first selectable neck angle 162.

The method can include the step of manufacturing a first porous casing 33 onto a first core body 34 so as to define a first femoral prosthesis 10 whereby 1) a first neck 28 extends out with respect to the proximal end of the first core body 34 at a fixed neck angle 40, and 2) the first porous casing 33 defines a first inner casing surface 108 that faces the first core body 34 and a first outer casing surface 110 opposite the first inner casing surface 108, wherein the first outer casing 33 extends along a first central outer casing axis 114, and the first neck 28 extends from the first core body 34 at a first selectable neck angle 162 with respect to the first central outer casing axis 114.

The method can include the step of manufacturing a second porous casing 33 onto a second core body 34 so as to define a second femoral prosthesis 10 whereby 1) a second neck 28 extends out with respect to the proximal end of the second core body 34 at the fixed neck angle 40, and 2) the second porous casing 33 defines a second inner casing surface 108 that faces the second core body 34 and a second outer casing surface 110 opposite the second inner casing surface 108, wherein the second outer casing 33 extends along a second central outer casing axis 114, and the second neck 28 extends from the second core body 34 at a second selectable neck angle 162 with respect to the second central outer casing axis 114 that is different than the first selectable neck angle 162.

Referring now to FIGS. 8A-8C, and as described above, the femoral prosthesis 10 can include the rotational position 166 with respect to the casing 33. Thus, the neck 28 can extend out from the core body 34 at the fixed neck angle 40 and at the selectable relative position 166 with respect to the outer casing surface 110. Further, because the inner casing surface 108 can extend along the outer core body surface 109, the neck 28 can extend out from the central inner casing axis 112 at the fixed neck angle 40 (see FIGS. 1-2B). As will now be described, the outer casing 33 can define the rotational position 166. For instance, the outer casing 33 can be fabricated such that the core 31, and thus the neck 28, can define any suitable selectable orientation with respect to the outer casing 33 about the axis of rotation 167. The axis of rotation 167 can be defined by the central core body axis 39, or can be offset from the central core body axis 39. As the inner core 31 defines the rotational position 166 is adjusted in a range of permissible rotational positions 166, the neck 28 defines a selectable position in a range of permissible selective positions that revolve about the axis of rotation 167.

The femoral prosthesis 10 can be customized such that the core body 34, and thus the core 31, can define any suitable rotational position 166 with respect to the axis of rotation 167. In particular, the casing 33 can be fabricated such that the core body 34 defines any suitable predetermined rotational position 166 with respect to the outer casing surface 110.

For instance, as illustrated in FIG. 8A, the core body 34 can define a first rotational position 166 within the casing 33. Thus, the core 31, including the neck 28, can similarly define the first rotational position 166. As illustrated in FIG. 8B, the core body 34 can define a second rotational position 166 within the casing 33 that is different than the first orientation. Thus, the core 31, including the neck 28, can similarly define the second rotational position 166. As illustrated in FIG. 8C, the core body 34 can define a third rotational position within the casing 33 that is different than each of the first and second rotational positions. Thus, the core 31, including the neck 28, can similarly define the third rotational position 166. The rotational positions 166 of the core body 34 within the casing 33 can be defined with respect to a sectional plan view that through both the core body 34 and the casing 33 and includes the anterior casing side 71 and the posterior casing side 73.

In some examples, the range of rotational positions 166 can be determined such that the at least a portion of the core body 34 is encapsulated by the casing 33 at all of the rotational positions 166 within the range of permissible rotational positions 166. The range of permissible rotational positions 166 can be determined such that the core body 34 does not protrude through the outer casing surface 110 at any of the rotational positions 166 in the range of permissible rotational positions 166. Further, the range of permissible rotational positions 166 can be determined such that a thickness 115 of the casing 33 at the anterior and posterior casing sides 71 and 73, respectively, can be maintained above a minimum thickness along an entirety of the anterior and posterior casing sides 71 and 73, respectively.

Referring now to FIGS. 8A-8B in particular, the range of rotational positions 166 can be defined by an angle of rotation 168. The angle of rotation 168 can be defined by a first selectable core body axis 169 and a second fixed casing axis 171. The first selectable core body axis 169 can extend from the medial core body side 54 and the lateral core body side 56. Further, the first selectable core body axis 169 can bisect each of the medial core body side 54 and the lateral core body side 56. These sides can be referred to as the medial core body side 54 and the lateral core body side 56 even when angulated about the axis of rotation 167, as they define the medial and lateral extent of the core body 34 when the core body 34 is in a neutral non-angulated position. It is recognized that the selectable core body axis 169 has an orientation that varies depending on the rotational position 166 of the core body 34. The second fixed casing axis 171 can extend from the outer casing surface 110 at the medial casing side 70 to the outer casing surface 110 at the lateral casing side 72. For instance, the second fixed casing axis 171 can bisect the outer casing surface 110 at the medial casing side 70 and the outer casing surface 110 at the lateral casing side 72. In one example, the angle of rotation 168 can be at least approximately 5 degrees up to at least approximately 15 degrees.

The range of rotational positions 166 as defined by the angle of rotation 168 can be a substantially 30 degree range. That is, the angle of rotation 168 can range up to approximately 15 degrees clockwise and approximately 15 degrees counterclockwise. For instance, the range of rotational positions 166 as defined by the angle of rotation 168 can be a substantially 20 degree range. That is, the angle of rotation 168 can range up to approximately 10 degrees clockwise and approximately 10 degrees counterclockwise. In some examples, the range of rotational positions 166 as defined by the angle of rotation 168 can be a substantially 20 degree range. That is, the angle of rotation 168 can range up to approximately 10 degrees clockwise and approximately 10 degrees counterclockwise. In other examples, the range of rotational positions 166 as defined by the angle of rotation 168 can be a substantially 10 degree range. That is, the angle of rotation 168 can range up to approximately 5 degrees clockwise and approximately 5 degrees counterclockwise. In still other examples, the range of rotational positions 166 as defined by the angle of rotation 168 can be a substantially 5 degree range. That is, the angle of rotation 168 can range up to approximately 2.5 degrees clockwise and approximately 2.5 degrees counterclockwise.

In this regard, it should be appreciated that the core body 34 can be sized substantially smaller than the footprint defined by the outer casing surface 110 to achieve a broader range of rotational positions 166. As the size of the core body 34 in the casing is increased with respect to the outer casing surface 110, the range of rotational positions 166 can decrease.

As illustrated in FIG. 8A, a first negative angle of rotation 168 can be counterclockwise, such that the core body 34 defines a negative first rotational position 166. The selectable first rotational position 166 in the range of rotational positions 166 can define a respective first anterior-posterior thickness profile of the casing 33. In particular, the casing 33 can define a thickness 115 along the length of the core body 34 that is a function of the rotational position 166 of the core body 34 relative to the casing 33. The thickness 115 of the casing 33 can extend from the inner casing surface 108 to the outer casing surface 110 at the anterior casing side 71 and the posterior casing side 73. As described above, the outer casing surface 110 can define at least a portion of the outer surface of the femoral prosthesis 10.

As the rotational position 166 of the core body 34 is varies, the thickness 115 of the anterior casing side 71 and the posterior casing side 71 can vary. When the core body 34 is in the first rotational position 166 illustrated in FIG. 8A, the thickness 115 of the casing 33 at the anterior casing side 71 can decrease as the anterior casing side 71 extends in the medial direction. Thus, the medial core body side 54 can be spaced a first distance from the outer casing surface 110 at the anterior casing side 71 along the anterior-posterior direction. In particular, the anterior side of the medial core body side 54 can be spaced the first distance from the outer casing surface 110 at the anterior casing side 71 along the anterior-posterior direction. The lateral core body side 56 can be spaced a second distance from the outer casing surface 110 at the anterior casing side 71 along the anterior-posterior direction. In particular, the anterior side of the lateral core body side 56 can be spaced the second distance from the outer casing surface 110 at the anterior casing side 71 along the anterior-posterior direction. The first distance can be different than the second distance when the core body 34 is angulated about the axis of rotation 167. In one example, for instance when the core body 34 is angulated to define the negative angle of rotation 168, the first distance can be less than the second distance.

Conversely, the thickness 115 of the casing 33 at the posterior casing side 73 can increase as the anterior casing side 71 extends in the medial direction. Thus, the medial core body side 54 can be spaced a third distance from the outer casing surface 110 at the posterior casing side 73 along the anterior-posterior direction. In particular, the posterior side of the medial core body side 54 can be spaced the third distance from the outer casing surface 110 at the posterior casing side 73 along the anterior-posterior direction. The lateral core body side 56 can be spaced a fourth distance from the outer casing surface 110 at the posterior casing side 73 along the anterior-posterior direction. In particular, the posterior side of the lateral core body side 56 can be spaced the fourth distance from the outer casing surface 110 at the posterior casing side 73 along the anterior-posterior direction. The third distance can be different than the fourth distance when the core body 34 is angulated about the axis of rotation 167. In one example, for instance when the core body 34 is angulated to define the negative angle of rotation 168, the third distance can be greater than the fourth distance. Further, the third distance can be substantially equal to the first distance, and the fourth distance can be substantially equal to the second distance. Alternatively, depending on the dimensions of the core body 34, the position of the core body 34 with respect to the anterior and posterior casing sides 71 and 73, respectively, and the location of the axis of rotation 167, the third distance can be different than the first distance, and the fourth distance can be different than the second distance. The first distance, the second distance, the third distance, and the fourth distance can be measured in a plane that is oriented substantially perpendicular to the central core body axis 39. The plane can bisect the core body 34 in some examples.

Referring now to FIG. 8B, a second positive angle of rotation 168 can be clockwise, and thus opposite the first negative angle of rotation 168 described above with respect to FIG. 8A. Thus, the core body 34 defines a positive second rotational position 166. The second rotational position 166 in the range of rotational positions 166 can define a respective second anterior-posterior thickness profile of the casing 33. In particular, when the core body 34 is in the second rotational position 166 illustrated in FIG. 8B, the thickness 115 of the casing 33 at the anterior casing side 71 can increase as the anterior casing side 71 extends in the medial direction. Thus, the medial core body side 54 can be spaced a first distance from the outer casing surface 110 at the anterior casing side 71 along the anterior-posterior direction. The lateral core body side 56 can be spaced a second distance from the outer casing surface 110 at the anterior casing side 71 along the anterior-posterior direction. The first distance can be different than the second distance when the core body 34 is angulated about the axis of rotation 167. In one example, for instance when the core body 34 is angulated to define the positive angle of rotation 168, the first distance can be greater than the second distance. direction Conversely, the thickness 115 of the casing 33 at the posterior casing side 73 can decrease as the anterior casing side 71 extends in the medial direction. Thus, the medial core body side 54 can be spaced a third distance from the outer casing surface 110 at the posterior casing side 73 along the anterior-posterior direction. The lateral core body side 56 can be spaced a fourth distance from the outer casing surface 110 at the posterior casing side 73 along the anterior-posterior direction. The third distance can be different than the fourth distance when the core body 34 is angulated about the axis of rotation 167. In one example, for instance when the core body 34 is angulated to define the negative angle of rotation 168, the third distance can be less than the fourth distance. Further, the third distance can be substantially equal to the first distance, and the fourth distance can be substantially equal to the second distance. Alternatively, depending on the dimensions of the core body 34, the position of the core body 34 with respect to the anterior and posterior casing sides 71 and 73, respectively, and the location of the axis of rotation 167, the third distance can be different than the first distance, and the fourth distance can be different than the second distance.

It should therefore be appreciated that when first and second femoral prostheses 10 define different rotational positions 166, the core 31 of second femoral prosthesis 10 is rotated about the axis of rotation 167 with respect to first femoral prosthesis 10. Further, the medial core body side 54 of the second femoral prosthesis 10 can be spaced further from the anterior casing side 71 than the medial core body side 54 of the first femoral prosthesis is spaced from the anterior casing side 71. The lateral core body side 56 of the first femoral prosthesis 10 can be spaced further from the anterior casing side 71 than the lateral core body side 56 of the first femoral prosthesis is spaced from the anterior casing side 71. The medial core body side 54 of the first femoral prosthesis 10 can be spaced further from the posterior casing side 73 than the medial core body side 54 of the second femoral prosthesis is spaced from the posterior casing side 73. The lateral core body side 56 of the second femoral prosthesis 10 can be spaced further from the posterior casing side 73 than the lateral core body side 56 of the first femoral prosthesis is spaced from the posterior casing side 73.

As illustrated in FIG. 8C, the core body 34 can be positioned in a first rotational position 166 with respect to the casing 33. For instance, the first rotational position 166 can define a neutral position whereby the thickness 115 of the anterior casing side 71 is substantially constant along the medial-lateral direction from the medial core body side 54 to the lateral core body side. Further, the thickness of the posterior casing side 73 can be substantially constant along the medial-lateral direction from the medial core body side 54 to the lateral core body side 56. Further, the medial and lateral core body sides 54 and 56, respectively, can be aligned along the medial-lateral direction. Additionally, the first selectable core body axis 169 can be substantially coincident with the second fixed casing axis 171.

With continuing reference to FIGS. 8A-8C, it should be appreciated a method can be provided for fabricating the femoral prostheses 10 that each includes the core body 34 that is configured to be inserted into the medullary canal 21 of the femur 23. The femoral prostheses 10 can include substantially equally sized and shaped core bodies 34 having different rotational position 166 in the respective casings 33. A method of fabricating the femoral prosthesis 10 can include the step of applying the porous casing 33 onto the core body 34 so as to define the inner casing surface 108 that faces the core body 34 and the outer casing surface 110 opposite the inner casing surface 108, such that the first selectable core body axis 169 defines a respective orientation with respect to the second fixed casing axis 171. For instance, the first selectable core body axis 169 can be angularly offset with respect to the second fixed casing axis 171 in a positive direction, a negative direction, or the first selectable core body axis 169 can be substantially coincident with the second fixed casing axis 171.

The method can include the step of manufacturing a first porous casing 33 onto a first core body 34 so as to define a first femoral prosthesis 10 whereby 1) a first neck 28 extends out with respect to the proximal end of the first core body 34 at a fixed neck angle 40, and 2) the first porous casing 33 defines a first inner casing surface 108 that faces the first core body 34 and a first outer casing surface 110 opposite the first inner casing surface 108. The first selectable core body axis 169 can define the respective orientation with respect to the second fixed casing axis 171. The method can further include fabricating a first femoral component 10 including the first porous casing and a first inner core 31 that includes the first core body 34 and the first neck 28.

The method can include the step of manufacturing a second porous casing 33 onto a second core body 34 so as to define a first femoral prosthesis 10 whereby 1) a second neck 28 extends out with respect to the proximal end of the second core body 34 at a fixed neck angle 40, and 2) the second porous casing 33 defines a second inner casing surface 108 that faces the second core body 34 and a second outer casing surface 110 opposite the second inner casing surface 108. The second selectable core body axis 169 can define the respective orientation with respect to the second fixed casing axis 171. The method can further include fabricating a first femoral component 10 including the first porous casing and a first inner core 31 that includes the first core body 34 and the first neck 28. The first and second femoral prostheses can further define different selectable neck angle 162 described above.

Referring now to FIGS. 9A-9B in particular, and as described above, the femoral prosthesis, can include a neck offset 164. For instance, the neck offset 164 can thus extend from the outer casing surface 110 of the outer casing 33 to the neck 28 substantially along the central neck axis 29. The neck offset 164 can be defined by a distance from the casing 33 to the neck 28 substantially along the central neck axis 29. In particular, the neck offset 164 can be defined by a distance from a proximal end of the casing 33 to the neck 28 substantially along the central neck axis 29. As will now be described, a position of the core body 34 in the casing 33 can determine the neck offset 164. For instance, the outer casing 33 can be fabricated such that the core body 34 can define any suitable position in the outer casing 33 that, in turn, determines the neck offset 164.

As illustrated in FIG. 9A, a first neck offset 164 from the neck 28 to the casing 33 substantially along the central neck axis 29 can define a first distance. When the core 31 includes the shoulder 32, the first distance can be defined by a minimum first neck offset 164 when the shoulder 32 abuts the casing 33. Thus, the first neck offset 164 can be defined as the dimension of the shoulder 32 substantially along the central neck axis 29. Alternatively, when the core 31 does not include the shoulder 32, then the first neck offset 164 can be defined by the dimension of the neck 28 along the central neck axis 29 when the neck 28 abuts the casing 33. Thus, the first neck offset 164 can be approximately zero in one examples. Alternatively, the neck 28 can be spaced from the outer casing surface 110 along the central neck axis 29 so as to define the first neck offset 164.

As illustrated in FIG. 9B, a second neck offset 164 from the neck 28 to the casing 33 substantially along the central neck axis 29 that is different than the first neck offset 164 of FIG. 9A. The second neck offset 164 can be greater than or less than the first neck offset 164. In the example illustrated in FIG. 9B, the second neck offset 164 is greater than the first neck offset 164. Further, because the neck 28 is positioned increasingly superiorly and medially as the neck offset 164 increases, the thickness 113 of the medial casing side 70 can decrease.

Thus, when a first femoral implant 10 or stem component 16 defines a first neck offset 164, and a second femoral implant 10 or stem component 16 defines a second neck offset 164 that is different than the first neck offset 164, a first thickness 113 of the medial casing side 70 from the inner casing surface 108 to the outer casing surface 110 is of the casing 33 of the first femoral implant 10 or stem component 16 is different than a second thickness 113 of the medial casing side 70 from the inner casing surface 108 to the outer casing surface 110 is of the casing 33 of the second femoral implant 10 or stem component 16. For instance, when the first neck offset 164 is greater than the second neck offset 164, the first thickness 113 can be greater than the second thickness 113. Conversely, when the first neck offset 164 is less than the second neck offset 164, the first thickness 113 can be less than the second thickness 113.

It should be appreciated that while the neck offset 164 can at least partially determine a position of the neck 28 with respect to the outer casing surface 110 substantially along the central neck axis 29, one or both of the selectable neck angle 162 and the rotational position 166 of the core body 34, and thus of the core 31, can further determine the position of the neck 28 and an orientation of the neck with respect to the outer casing surface 110. Because the trunnion 30 extends from the neck 28 and is configured to be coupled to the head component 18, one or more up to all of the neck offset 164, the selectable neck angle 162, and the rotational position 166 of the core body 34 can determine the position and orientation of the head component 18 relative to the outer casing surface 110, and thus relative to the femur.

With continuing reference to FIGS. 9A-9B, it should be appreciated a method can be provided for fabricating the femoral prostheses 10 that each includes the core body 34 that is configured to be inserted into the medullary canal 21 of the femur 23. The femoral prostheses 10 and in particular the stem components 16, can include substantially equally sized and shaped cores 31, but disposed in different locations in the respective outer casings 33 along the central neck axis 29 so as to define different neck offsets 164. A method of fabricating the femoral prosthesis 10 can include the step of applying the porous casing 33 onto the core body 34 so as to define the inner casing surface 108 that faces the core body 34 and the outer casing surface 110 opposite the inner casing surface 108, such that the neck 28 is offset from the casing 33 as desired.

The method can include the step of manufacturing a first porous casing 33 onto a first core body 34 so as to define a first femoral prosthesis 10 whereby 1) a first neck 28 extends out with respect to the proximal end of the first core body 34 at a fixed neck angle 40, and 2) the neck 28 defines a fixed distance to the core body 34. The first porous casing 33 defines a first inner casing surface 108 that faces the first core body 34 and a first outer casing surface 110 opposite the first inner casing surface 108. The first femoral prosthesis can define the first neck offset 164 as described above.

The method can include the step of manufacturing a second porous casing 33 onto a second core body 34 so as to define a first second femoral prosthesis 10 whereby 1) a second neck 28 extends out with respect to the proximal end of the second core body 34 at the fixed neck angle 40, and 2) the second neck 28 defines the fixed distance to the core body 34. The second porous casing 33 defines a second inner casing surface 108 that faces the second core body 34 and a second outer casing surface 110 opposite the second inner casing surface 108. The second outer casing surface 110 can be substantially equally sized and shaped with respect to the first outer casing surface 110. The second femoral prosthesis 10 can define the second neck offset 164 as described above. Alternatively or additionally, the first femoral prosthesis 10 can include either or both of the first selectable neck angle 162 and the first rotational position 166 described above. Alternatively or additionally still, the first femoral prosthesis 10 can include either or both of the first selectable neck angle 162 and the first rotational position 166 described above.

With continuing reference to FIGS. 9A-9B, while the neck offset 164 provides one way to measure the different positions of substantially identical cores 31, in still other examples the different positions can be defined by an offset from the casing 33, and in particular from the proximal casing end 151, to a portion 173 of the core 31 that includes the neck 28 and the trunnion 30. The portion 173 of the core 31 can further include the shoulder 32. As described above with respect to the neck offset 164, the offset from the casing 33 to the portion of the core 31 can be oriented along a direction substantially parallel to the central neck axis 29.

In this regard, it is recognized that a plurality of femoral prostheses can be designed and manufactured having substantially identical core bodies 34 that define different geometries when surrounded by respective casings 33. The casings 33 can be additively manufactured onto the core bodies 34. Alternatively, the casings 33 can be separately fabricated so as to receive the respective core bodies 34. The geometries can be selected as one or more up to all of the selectable neck angle 162 (see FIGS. 7B-7C), the rotational position 166 and resulting angle of rotation 168 (see FIGS. 8A-8C), and the neck offset 164 (see FIGS. 9A-9B).

Figure 10:
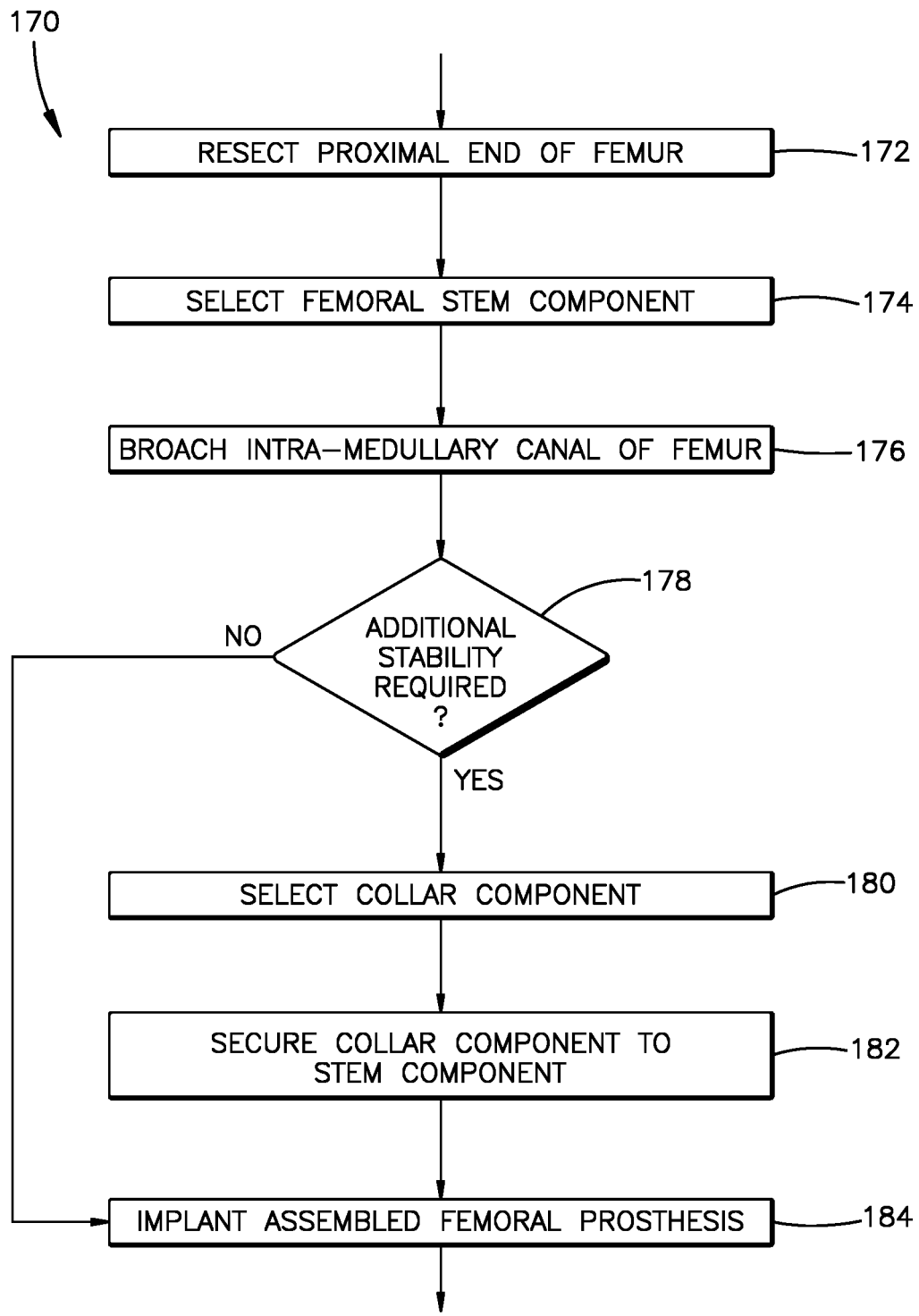
FIG. 10 is a simplified block diagram of a method for implanting a femoral prosthesis illustrated in FIG. 1.

Referring now to FIG. 10, a method 170 for performing a hip arthroplasty is shown. The method 170 includes step 172, in which an orthopaedic surgeon, or other member of a surgical team, may resect a proximal end of a patient's femur 23 to form the surgically prepared planar proximal surface 90. As described above, the femoral prosthesis 10 may include a stem component 16 and a femoral head component 18. Depending on the needs of the patient, the surgeon may also include the collar 14, including one of the stabilizing collar 22 or trochanter collar 24 in the femoral prosthesis 10. Alternatively, the femoral prostheses as fabricated can include the collar 14. In some embodiments, such as the case in some revision hip arthroplasties, an orthopaedic surgeon will also prepare medial surface of a trochanter of the patient's femur 23. At step 174, the orthopaedic surgeon selects a stem component 16 and a femoral head component 18 based on surgical parameters determined before the surgical operation began and intraoperative data determined during the surgical operation. For instance, the stem component 16 can be any one of the first stem component that includes the first core body encased by the casing 33, the second stem component that includes the second core body encased by the casing 33, and the third stem component that includes the second core body encased by the casing 33 as described above with respect to FIGS. 7A-7C.

At step 176, the orthopaedic surgeon may insert a broach through the planar proximal surface 90 of the patient's femur 23 to define a passageway in the medullary canal 21 of the patient's femur 23 sized to receive the selected femoral stem component 16 (see FIGS. 2A-2B). The size of the broach used by the orthopaedic surgeon is determined based on the size of the selected femoral component.

At step 178, the orthopaedic surgeon determines whether the femoral prosthesis 10 requires more stability than what is provided by the stem component 16 alone. If the femoral prosthesis 10 does not indicate desirability for additional stability, the surgeon may continue to step 174 in which the stem component 16 and the femoral head component 18 are implanted in the patient's femur 23. If additional stability is desired, the surgeon continues to step 180 in which the surgeon selects a collar from the plurality of collars 14 to couple to the stem component 16. Alternatively, the surgeon can select a femoral prosthesis that was manufactured with a collar 14. Each of the collars of the plurality of collars includes the inferior surface 103 (see FIG. 2A) configured to engage the planar proximal surface 90 of the patient's femur 23. The plurality of collars 14 may include a number of different types of collars configured to provide different types of stability. For example, the stabilizing collar 22 includes a platform that provides a large surface area to engage the planar proximal surface 90 of the patient's femur 23. In another example, the trochanter collar 24 includes an abutment member 104 configured to couple a trochanter of the patient's femur 23 to the femoral prosthetic assembly.

At step 182, the orthopaedic surgeon may secure the selected collar to the stem component 16 such that the inferior surface 103 of the collar extends transversely to the central core body axis 39. At step 184, once the selected collar 14 is secured in a fixed position relative to the stem component 16, the assembled femoral prosthesis 10 is positioned and implanted in the patient's femur 23 such that the inferior surface 103 of the selected collar engages with the planar proximal surface 90 of the patient's femur 23.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A femoral prosthesis comprising:
an elongate core body that extends along a central core body axis from a proximal core body end to a distal core body end opposite the proximal core body end, the core body including a medial core body side and a lateral core body side opposite the medial core body side, the medial and lateral core body sides extending from the proximal core body end to the distal core body end, wherein the core body is configured to be received in a medullary canal of a femur;
a neck that extends out with respect to the proximal core body end; and
a porous casing that encases at least a portion of the core body, wherein the porous casing defines an inner casing surface that faces the core body and an outer casing surface opposite the inner casing surface,
wherein the inner surface of the porous casing extends along a central inner casing axis that is substantially coincident with the central core body axis, and the outer surface of the porous casing extends along a central outer casing axis that intersects the central inner casing axis within an outer perimeter of the core body with respect to a side elevation view of the femoral prosthesis that includes the proximal core body end, the distal core body end, the medial core body side, and the lateral core body side,
wherein the porous casing defines a thickness from the inner casing surface to the outer casing surface, the thickness at a first side of the porous casing increases as the casing extends in a distal direction from the proximal core body end to the distal core body end, and the thickness at a second side of the porous casing decreases as the casing extends in the distal direction, and the second side is opposite the first side.

2. The femoral prosthesis of claim 1, wherein the core body and the neck define a single monolithic component.

3. The femoral prosthesis of claim 1, wherein the porous casing is an additively manufactured porous casing.

4. The femoral prosthesis of claim 1, further comprising a porous collar that is configured to extend out with respect to the neck in a predetermined direction.

5. The femoral prosthesis of claim 1, wherein the neck extends out with respect to the proximal core body end along a central neck axis that defines a fixed neck angle with respect to the central core body axis, and the central neck axis defines a selectable neck angle with respect to the central outer casing axis, wherein the selectable neck angle is different than the fixed neck angle.

6. The femoral prosthesis of claim 5, wherein the selectable neck angle is within a range greater than zero degrees up to approximately 30 degrees.

7. The femoral prostheses of claim 1, wherein the porous casing further defines a rotational position of the core body relative to the outer casing surface about the central core body axis.

8. The femoral prosthesis of claim 1, wherein the first side defines a medial side of the porous casing, and the second side defines a lateral side of the porous casing.

9. A femoral prosthesis comprising:
an elongate core body that extends along a central core body axis from a proximal core body end to a distal core body end opposite the proximal core body end, the core body including a medial core body side and a lateral core body side opposite the medial core body side, the medial and lateral core body sides extending from the proximal core body end to the distal core body end, wherein the core body is configured to be received in a medullary canal of a femur;
a neck that extends out with respect to the proximal core body end; and
a porous casing that encases at least a portion of the core body, wherein the porous casing defines an inner casing surface that faces the core body and an outer casing surface opposite the inner casing surface,
wherein the inner surface of the porous casing extends along a central inner casing axis that is substantially coincident with the central core body axis, and the outer surface of the porous casing extends along a central outer casing axis that intersects the central inner casing axis within an outer perimeter of the core body with respect to a side elevation view of the femoral prosthesis that includes the proximal core body end, the distal core body end, the medial core body side, and the lateral core body side,
wherein the neck extends out with respect to the proximal core body end along a central neck axis that defines a fixed neck angle with respect to the central core body axis, and the central neck axis defines a selectable neck angle with respect to the central outer casing axis, wherein the selectable neck angle is different than the fixed neck angle.

10. The femoral prosthesis of claim 9, wherein the selectable neck angle is within a range greater than zero degrees up to approximately 30 degrees.

11. The femoral prosthesis of claim 9, wherein the core body and the neck define a single monolithic component.

12. The femoral prosthesis of claim 9, wherein the porous casing is an additively manufactured porous casing.

13. The femoral prosthesis of claim 9, further comprising a porous collar that is configured to extend out with respect to the neck in a predetermined direction.

14. The femoral prostheses of claim 9, wherein the porous casing further defines a rotational position of the core body relative to the outer casing surface about the central core body axis.

15. The femoral prosthesis of claim 9, wherein the outer casing surface is nonparallel with respect to the inner casing surface.

16. The femoral prosthesis of claim 15, wherein:
the porous casing defines a thickness from the inner casing surface to the outer casing surface, the thickness at a first side of the porous casing increases as the casing extends in a distal direction from the proximal core body end to the distal core body end, and the thickness at a second side of the porous casing decreases as the casing extends in the distal direction, and the second side is opposite the first side, and
the first side of the porous casing defines a medial side of the porous casing, and the second side defines a lateral side of the porous casing.

* * * * *